(12) United States Patent
Jenkins et al.

(10) Patent No.: US 10,085,436 B2
(45) Date of Patent: Oct. 2, 2018

(54) COMPOSITIONS AND METHODS FOR BED BUG CONTROL USING ENTOMOPATHOGENIC FUNGI

(71) Applicant: THE PENN STATE RESEARCH FOUNDATION, University Park, PA (US)

(72) Inventors: Nina E. Jenkins, State College, PA (US); Alexis M. Barbarin, Philadelphia, PA (US); Edwin G. Rajotte, State College, PA (US); Matthew B. Thomas, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 69 days.

(21) Appl. No.: 14/810,137

(22) Filed: Jul. 27, 2015

(65) Prior Publication Data

US 2015/0327533 A1 Nov. 19, 2015

Related U.S. Application Data

(62) Division of application No. 13/755,360, filed on Jan. 31, 2013, now abandoned.

(60) Provisional application No. 61/593,025, filed on Jan. 31, 2012.

(51) Int. Cl.
*A01M 1/20* (2006.01)
*A01M 1/10* (2006.01)
*A01N 25/00* (2006.01)
*A01N 25/04* (2006.01)
*A01N 25/08* (2006.01)
*A01N 65/00* (2009.01)
*A01N 63/04* (2006.01)

(52) U.S. Cl.
CPC .......... *A01M 1/2011* (2013.01); *A01M 1/103* (2013.01); *A01N 25/002* (2013.01); *A01N 25/04* (2013.01); *A01N 25/08* (2013.01); *A01N 63/04* (2013.01); *A01N 65/00* (2013.01)

(58) Field of Classification Search
CPC ........ A01N 25/08; A01N 65/00; A01N 63/04; A01N 25/04; A01N 25/002; A01N 25/34; A01M 1/103; A01M 1/2011
See application file for complete search history.

(56) References Cited

U.S. PATENT DOCUMENTS

| | | | |
|---|---|---|---|
| 5,683,689 A | 11/1997 | Stimac et al. | |
| 5,939,065 A * | 8/1999 | Bradley | A01N 63/04 424/93.5 |
| 6,254,864 B1 * | 7/2001 | Stimac | A01N 25/006 424/405 |
| 6,403,085 B1 | 6/2002 | Stimac | |
| RE38,958 E | 1/2006 | Stimac et al. | |
| 7,122,176 B2 | 10/2006 | Stamets | |
| 8,053,223 B2 | 11/2011 | Meikle et al. | |
| 2002/0146444 A1 | 10/2002 | Bradley et al. | |
| 2009/0074809 A1 | 3/2009 | Jackson et al. | |
| 2010/0112060 A1 | 5/2010 | Maor et al. | |
| 2010/0317614 A1 | 12/2010 | Bachelet et al. | |
| 2011/0038839 A1 | 2/2011 | Jackson et al. | |
| 2011/0070308 A1 | 3/2011 | Williams et al. | |
| 2011/0280839 A1 | 11/2011 | Ford | |
| 2011/0311603 A1 * | 12/2011 | Lucas | A01N 25/34 424/411 |
| 2012/0039976 A1 | 2/2012 | Stamets | |
| 2012/0070414 A1 * | 3/2012 | Stamets | A01N 63/04 424/85.5 |

FOREIGN PATENT DOCUMENTS

| | | | |
|---|---|---|---|
| CN | 101502272 | 8/2009 | |
| CN | 101861878 | 10/2010 | |
| GB | 2255018 | 10/1992 | |
| MX | 2011011479 | 11/2011 | |
| RU | 2048097 | 11/1995 | |
| WO | WO 2008095016 A2 * | 8/2008 | ........... A01N 25/006 |
| WO | WO 2010044680 A1 * | 4/2010 | ............ A01N 63/04 |
| WO | WO 2011037448 A1 * | 3/2011 | ............. A01N 25/04 |
| WO | 2014117118 | 7/2014 | |

OTHER PUBLICATIONS

Beg Bug Exterminators—"Bed Bugs." Retrieved May 15, 2016. Retrieved from internet <URL: http://www.bedbugs.org/beg-bugs-exterminators/>.*
Bug Guide (published online Apr. 23, 2005). "Species Cimex Lectularius—Common Beg Bug". Retrieved May 16, 2016. Retrieved on the internet <URL: http://bugguide.net/node/view/15475>.*
Anderson, Robert D. et.al, "Comparative growth kinetics and viruience of four different isolates of entomopathogenic fungi in the house fly (Musca domestica L.)", Journal of Invertebrate Pathology, 107 (Apr. 21, 2011), pp. 179-184.
Blanford, Simon et. al., Fungal Pathogen Reduces Potential for Malaria Transmission:, Science magazine, Jun. 10, 2005, vol. 308, pp. 1638-1641.

(Continued)

*Primary Examiner* — Doan Thi-Thuc Phan
(74) *Attorney, Agent, or Firm* — McDermott Will & Emery LLP

(57) ABSTRACT

Barrier treatment compositions using conidia of entomopathogenic fungi and methods for applying and using the same for bed bug population control and prevention are disclosed. The compositions and methods of the invention provide residual biopesticides control for bed bug populations using barrier treatment compositions transferring conidia of entomopathogenic fungi to a population of bed bugs providing effective kill within about 24 hours to about 10 days. The compositions and methods provide significantly enhanced horizontal transmission of the conidia of the entomopathogenic fungi providing enhanced bed bug control without detrimental effects of bed bug tolerance, resistance and/or negative impact on humans or animals contacting the residual biopesticides.

19 Claims, 19 Drawing Sheets

(56) References Cited

OTHER PUBLICATIONS

Blanford, Simon et. al., "Lethal and Pre-Lethal Effects of a Fungal Biopesticide Contribute to Substantial and Rapid Control of Malaria Vectors" PLoS ONE, Aug. 29, 2011, vol. 6, Issue 8, e23591, 11 pages.
Busvine, James R., Insecticide-Resistance in Bed-Bugs:, Bull. Wld Hlth Org. 19, (6) pp. 1041-1052, 1958.
Coleman, Michael, et. al., "Insecticide resistance monitoring and evaluation in disease transmitting mosquitoes" J. Pestic. Sci. 32(2) 2007, pp. 69-76.
Darbro, Jonathan M. et. al., "Spore Persistence and Likelihood of Aeroallergenicity of Entomopathogenic Fungi Used for Mosquito Control", Am. J. Trop. Med. Hyg. 80(6), Feb. 12, 2009, pp. 992-997.
Elkinton, J.S. et. al., "Distribution &Apparent Spread of Entomophaga Maimaiga (Zygomycetes: Entomophthorales) in Gypsy Moth (Lepidoptera: Lymantriidae) Populations in No. America", Entomological Society of America, Aug. 12, 1991, vol. 20, No. 6, pp. 1601-1605.
Gillespie, Adrain T. et. al. "The Use of Entomogenous Fungi for Pest Control and the Role of Toxins in Pathogenesis*", Pestic. Sci., May 17, 1989, pp. 203-215.
Hajek, Ann E. et. al., "Introduction and Spread of Fungal Pathogen Entomophaga maimaiga (Zygomycetes: Entomophthorales) Along the Leading Edge of Gypsy Moth (LepidopteraL Lymantriidae) Spread", 1996 Entomological Society of America, pp. 1235-1247.
Hancock, P.A., et. al. "An age-structured model to evaluate the potential of novel malaria-control interventions: a case study of fungal biopesticide sprays", Proc. R. Sco. B (2009) 276, pp. 71-70.
Howard, Anabel FV et. al., "The entomopathogenic fungus Beauveria bassiana reduces instaneous blood feeding in wild multi-insecticide-resistant Culex quinquefasciatus mosquitos in Benin, West Africa", Parasites & Vectors, 2010, 3:87.
Hwang, Stephen W. et. al., "Bed Bug Infestations in an Urban Enviroment", Emerging Infectious Diseases, vol. 11, No. 4, Apr. 2005, pp. 533-538.
Kikakie, Christopher K. et. al., "The infectivity of the entomopathogenic fungus Beauveria bassiana to insecticide-resistant and suscptible Anopheles arabiensis mosquitoes at two different temperatures", Malaria Journal 2010, 9:71.
Koella, Jacob C. et. al. "Towards evolution-proof malaria control with insecticides", Evolutionary Applications, 2009 Blackwell Publishing Ltd (Apr. 27, 2009), pp. 169-480).
Lomer, C. J. et. al. "Biological Control of Locusts and Grasshoppers", Annu. Rev. Entomol. 2001, 46:667-702.
Milner, R. J., "Prospects for Biopesticides for Aphid Control" Entomophaga 42 (1/2) 1997, pp. 227-239.
Moore, David, J. et. al., "Laboratory Evaluations of Insecticide Product Efficacy for Control of Cimex lectularius" Journal of Economic Entomology, 99(6), pp. 2080-2086, 2006.
Pedrini, Nicolas et. al., "Control of Pyrethroid-Resistant Chagas Disease Vectors with Entomopathogenic Fungi", PLoS Neglected Tropical Diseases, May 12, 2009, vol. 3, Issue 5, e434, pp. 1-11.
Penn State, College of Agricultural Sciences, Cooperative Extension, Entomological Notes, Department of Entomology, "Bed Bugs Cimex Lectularius L" Apr. 2003, 2 pages.
Potter, Michael, F. "A Bed Bug State of Mind" PCT Magazine, Oct. 2005, 6 pages.
Reinhardt, Klaus et. al., "Biology of the Bed Bugs (Cimicidae)" Annu. Rev. Entomol., Sep. 1, 2006, 52:351-74.
Romero, Alvaro et. al., "Insecticide Resistance in the Bed Bug: A Factor in the Pest's Sudden Resurgence?" Journal of Medical Entomology, 44(2):175-178, 2007.
Scholte, Ernst-Jan et. al., "Pathogenicity of five east African entomopathogenic fungi against adust Anopheles gambiae s.s. mosquitoes (Diptera, Cullcidae)", Proc. Exper. Appl. Entomol. NEV Amnsterdam, vol. 14, 2003, pp. 25-29.
Scholte, Ernst-Jan et. al., Infection of malaria (Anopheles gambiae s.s.) and filariasis (Culex quinquefasciatus) vectors with the entomopathogenic fungus Metarhizium anisopliae:, Malaria Journal, Sep. 15, 2003, 2:29, pp. 1-8.
Seong, Keon Mook et.al., "Establishment of Quantitative Sequencing and Filer Contact Vial Bioassay for Monitoring Pyrethroid Resistance in the Common Bed Bug, Cimex lectularius", Journal of Medical Entomology, 47(4): 592-599, 2010.
Thomas, Matthew B., et. al., "Fungal bioinsecticide with a sting" Nature Biotechnology, vol. 25, No. 12, Dec. 2007, pp. 1367-1368.
Thomas, Matthew B. et. al., Biological Control of Locust and Grasshoppers Using a Fungal Pathogen: The Importance of Secondary Mar. 22, 1995.
Yeo, Helen, et.al. "Laboratory evaluation of temperature effects on the fermination and growth of entomopathogenic fungi and on their pathogenicity to two aphid species", Pest Managment Science, 59:156-165 (Online:2003).
Yoon, Kyong Sup et al., "Biochemical and Molecular Analysis of Deltamethrin Resistance in the Commen bed Bug (Hemiptera: Cimicidae:" Journal of Medical Entomology, 45(6): 1092-1101, 2008.
Zimmerman, Gisbert, "Review of safety of entomopathogenic fungi Beauveria bassiana and Beauveria brongniartii", Biocontrol Science and Technology, Jul. 5, 2007; 17(5/6): pp. 553-596.
Zimmerman, Gisbert, "Reiview of safety of entomopathogenic fungus Metarhizium anisophliae", Biocontrol Science and Technology, 2007; 17(9): pp. 879-920. Dec. 31, 2007.
Miller, Dini, M., "Bed Bug Treatment Using Insecticides", Virginia Tech, pp. 1-4, http://consensus.fsu.edu/DACS/bbwg/Bed%20bug%Treatment%20Using%20Chemicals%20(Virginia%20Tech).pdf [retrieved from Internet on Jan. 10, 2013].
Pereira, Roberto, et. al., "Bed Bugs: Containerized fumigation and heat treatment", University of Florida, Sep. 2008, pp. 1-100, http://entnemdept.ifas.ufl.edu/sepmc/Bed_Bug_Manual.pdf [retrieved from Internet on Jan. 10, 2013].
Polanco, Andrea M. et. al., "Population Growth Potential of the Bed Bug, Cimex lectularious L.: A Life Table Anaylis", Insects 2011, 2, 173-185.
Johnson, C.G., "The Ecology of the Bed-Bug, Cimex Lectularius L., in Britian: Report on Research, 1935-40", The Journal of Hygiene, vol. 41, No. 4 (Dec. 1941), pp. 345-461.
International Searching Authority,"International Search Report and The Written Opinion" issued in connection to International Application No. PCT/US2013/024035 dated Jun. 14, 2013.

* cited by examiner

COMPOSITIONS AND METHODS FOR BED BUG CONTROL USING ENTOMOPATHOGENIC FUNGI

CROSS-REFERENCE TO RELATED APPLICATIONS

This application is a Divisional application of U.S. Ser. No. 13/755,360 filed Jan. 31, 2013, which claims priority to U.S. Provisional Application No. 61/593,025, filed Jan. 31, 2012, all of which are herein incorporated by reference in their entirety.

FIELD OF THE INVENTION

The invention relates to compositions and methods, including prophylactic methods, for bed bug control using entomopathogenic fungi. In particular, the compositions and methods of the invention provide residual biopesticide control for bed bug populations using barrier treatment compositions. The barrier treatment compositions may optionally include a host and/or artificial lure and/or trap to attract bed bug populations. The efficacy of the compositions and methods are significantly enhanced due to the horizontal transmission of conidia spores of the entomopathogenic fungi.

BACKGROUND OF THE INVENTION

The human bed bug *Cimex lectularius* is a hematophagous insect that requires a blood meal for growth and development. Over the past decade, bed bug infestations have grown virtually exponentially in both North America and Europe (Hwang et al., (2005) Emerging Infectious Diseases 11(4), 533-538). Although the exact conditions prompting the recent resurgences is uncertain, the rise in bed bug infestations nationwide has been linked to increased international travel, changes in pest management practices, and increased insecticide resistance (Romero et al., Journal of Medical Entomology 44(2), 175-178 (2007); Potter, Pest Control Technology 33, (2005)).

Current bed bug control measures rely heavily on the use of pyrethroid insecticides. However, increased insecticide resistance threatens bed bug control efforts throughout the world (Moore and Miller, (2006). Journal of Economic Entomology 99, 2080-2086; Romero et al., 2007; Yoon et al., Journal of Medical Entomology 4, 1092-1101 (2008); Seong et al., Journal of Medical Entomology 47, 592-599 (2010)). In addition to pyrethroids, bed bugs are known to be resistant to DDT in Israel (Levinson, Riv. Parassit., 14, 233 (1953)), French Guiana (Floch, Rapp. Institut Pasteur de la Guyane, p. 152 (1955)), Greece, Italy, China, and Iran (Busvine, Bull. World Health Organization 19, 1041-1052 (1958)). Bed bugs demonstrate significant agility and evolutionary resistance to various chemical insecticides and pesticides. Pesticide resistance is a major reason for the recent bed bug resurgence (Potter, 2005). In addition, pesticide resistance results in increased application rates and frequencies that unnecessarily expose humans and animals to these toxins. Due to the impact of insecticide resistance, there is potential for developing alternative methods of bed bug control.

One such alternative is the formulation of entomopathogens as biopesticides. With their documented low mammalian toxicity (Zimmerman, Biocontrol Sci. Technol., 17: 553-596 (2007) and Zimmerman, Biocontrol Sci. Technol., 17: 879-920 (2007)) entomopathogenic fungi have great potential for development as components of a comprehensive integrated pest management approach that includes pest monitoring, sanitation and resident education.

The entomopathogenic fungus *Beauveria bassiana* is capable of infecting a broad range of insect hosts and has been used in horticulture, agriculture, mosquito control, and soil insect control. In the past, entomopathogenic fungi have been used to control agriculture and forest pests including the gypsy moth *Lymantria dispar* (Elkinton et al., Environmental Entomology 20, 1601-1605 (1991); Hajek et al., Journal of Environmental Entomology 25, 1235-1247 (1996)), and various species of aphids (Hall, Microbial control of pests and plant diseases 1970-1980. Academic Press, London, pp 483-498 (1981); Milner, Entomophaga 42, 227-23 (1997); Yeo et al., Pest Management Science 59, 156-165 (2003)), and locusts (Lomer et al, Annual Review of Entomology 46, 667-702 (2001)).

In addition, recent research has illustrated the effectiveness of entomopathogenic fungi on blood feeding insects and disease vectors including *Triatoma infestans* (Pedrini et al., Neglected Tropical Diseases 3(2), 1-11 (2009)) and several species of mosquito (Blanford et al., Science 308, 1638-1641 (2005); Blanford et al., PLoS One. 6(8): e23591 (2011)). Once germinated, the conidia of entomopathogenic fungi penetrate directly through the cuticle of the insect. Once inside, the fungus produces metabolites that kill the insect as a result of nutrient sequestration and internal mechanical damage (Gillespie and Clayton, Pesticide Science 27, 203-215 (1989)).

Importantly, it has been shown that insecticide resistance confers no cross-resistance to entomopathogenic fungi in mosquitoes (Farenhorst et al., PNAs 106(41), 17443-17447 (2008); Blanford et al., 2011). In addition, research on mosquitoes suggests that fungal infection leads to insect death beginning at day three (Scholte et al., Proceedings of the Section Experimental and Applied Entomology of the Netherlands Entomological Society (NEV) 14, 25-29 (2003); Blanford et al., 2005). Since this kill time is slow compared to pesticides, fungal infected insects may have the opportunity to reproduce, which could reduce selection pressure for insecticide resistance (Hancock et al., Proceedings of the Royal Society of London B 276, 71-80 (2009); Koella et al., Evolutionary Applications 2: 469-480 (2009)). Understanding bed bug susceptibility to biopesticides can have important implications in bed bug management practices.

There remains a significant need for improved bed bug management practices. Current infestations of bed bugs can result in significant costs, including for example, direct cost of treatments (insecticides and/or pesticides, fuming, cleaning, laundering, etc.), and indirect costs (e.g. lost profits). For example, an infestation of a hotel room with bed bugs requires the use of insecticides, heat or cold treatment, and/or fumigation. This generally requires vacating and treating the infested room and all surrounding rooms (including above and below) due to the risk of harborages in adjoining infrastructures. In addition, there are also significant psychological effects of having a bed bug infestation. As a result, there is significant need for less time consuming and more efficacious treatments, along with prophylactic measures for preventing bed bug infestations.

Accordingly, it is an objective of the claimed invention to develop compositions and methods for use in employing entomopathogenic fungi for controlling bed bug populations and/or preventing bed bug infestations.

A further object of the invention are compositions and methods for using entomopathogenic fungi to control and/or prevent bed bug populations of various feeding statuses, sexes, strains, exposure substrates, and at varying life history stages.

A further object of the invention is compositions and methods for using entomopathogenic fungi as a superior alternative mode of action for bed bug control and/or prophylaxis in comparison to pyrethroid, resulting in the reduction of pyrethroid resistance in bed bugs.

A still further object of the invention is to provide compositions and methods for bed bug population control and/or prophylaxis that are superior to standard chemical treatments, as a result of targeting all concealed harborages in established infestations through the horizontal transmission of entomopathogenic fungi. These and other aspects of the invention are set forth in further detail within the description of the invention.

BRIEF SUMMARY OF THE INVENTION

An advantage of the invention is effective use of entomopathogenic fungi for controlling all life stages of bed bugs to improve eradication of a population of bed bugs, along with prophylactic biopesticide treatment options. A further advantage of the invention is provided as a result of the methods of administration and use requiring only short-term exposure to a surface in order to provide a lethal dose. Still further, the present invention provides sprayed surfaces that are stable for extended periods of time allowing for spore survival and prolonged efficacy for the control and/or prophylaxis of bed bugs.

According to an embodiment of the invention, the invention discloses a barrier treatment composition for bed bug control and/or prophylaxis comprising: a substrate surface; a source of an entomopathogenic fungi formulated in oil or an oil-based aqueous mixture or suspension; and an optional natural or artificial lure to attract bed bugs to said barrier treatment composition. In an aspect, the entomopathogenic fungus is a viable source of fungal conidia, and conidia applied onto the substrate surface to create the barrier treatment composition having a concentration of at least about 100 conidia/cm$^2$. In a further aspect, the oil formulation is odorless and clear.

According to a further embodiment of the invention, the invention discloses a method for controlling and/or preventing bed bug populations using a biopesticide comprising: providing a barrier treatment composition comprising a substrate surface treated with entomopathogenic fungal conidia formulated in oil or an oil-based aqueous mixture or suspension, wherein said entomopathogenic fungi produce a viable source of fungal conidia which is applied onto the substrate surface to create the barrier treatment composition having a concentration of at least about 100 conidia/cm$^2$; contacting a portion of a bed bug population with the barrier treatment composition, wherein the contact is the bed bug crossing the surface; causing the horizontal transmission of the conidia to an additional population of bed bugs; killing the first and second populations of bed bugs; and providing residual or prophylactic protection against additional bed bug populations.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
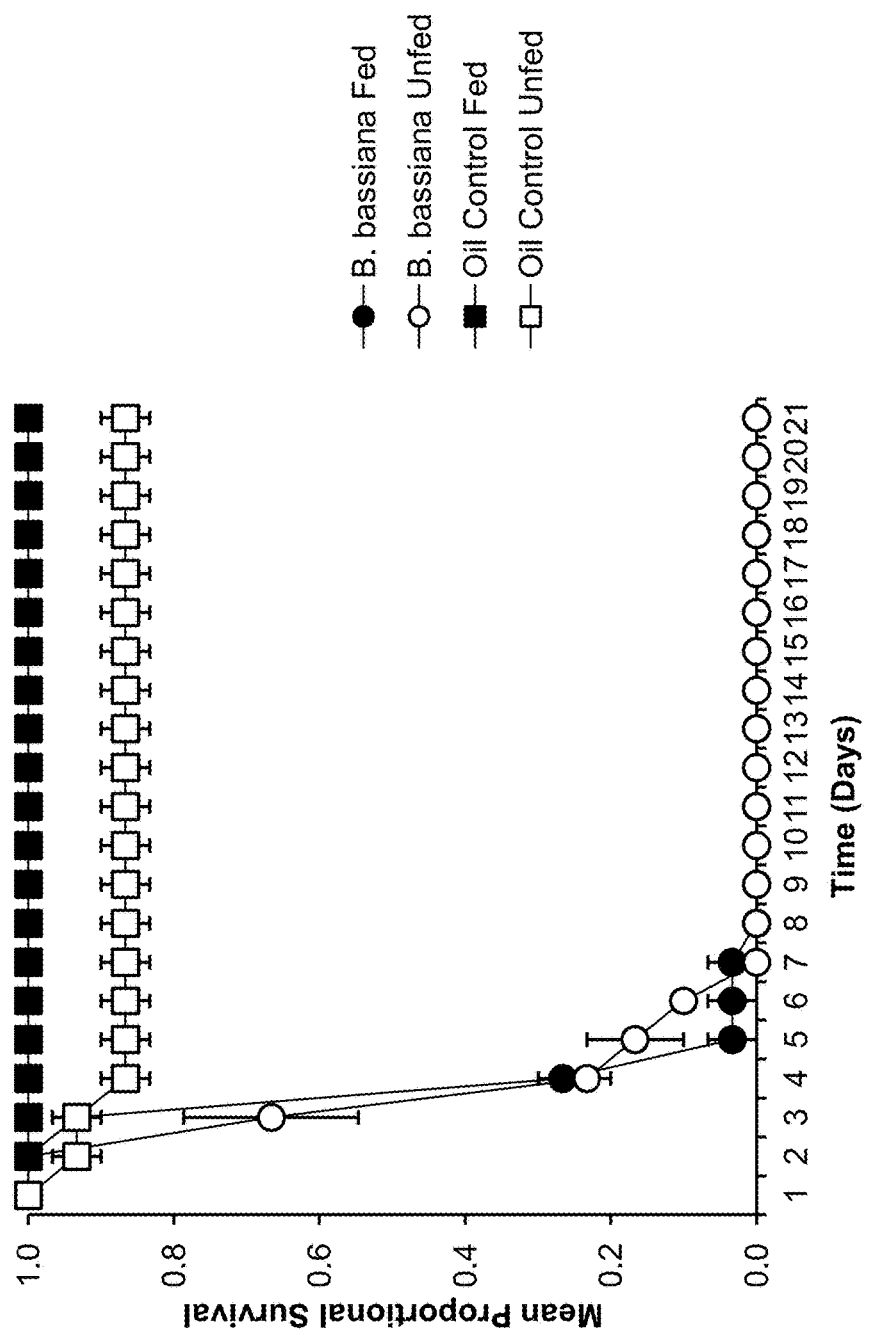
FIG. 1 is a graph showing no difference in bed bug susceptibility due to feeding status according to an embodiment of the invention.
Figure 2:
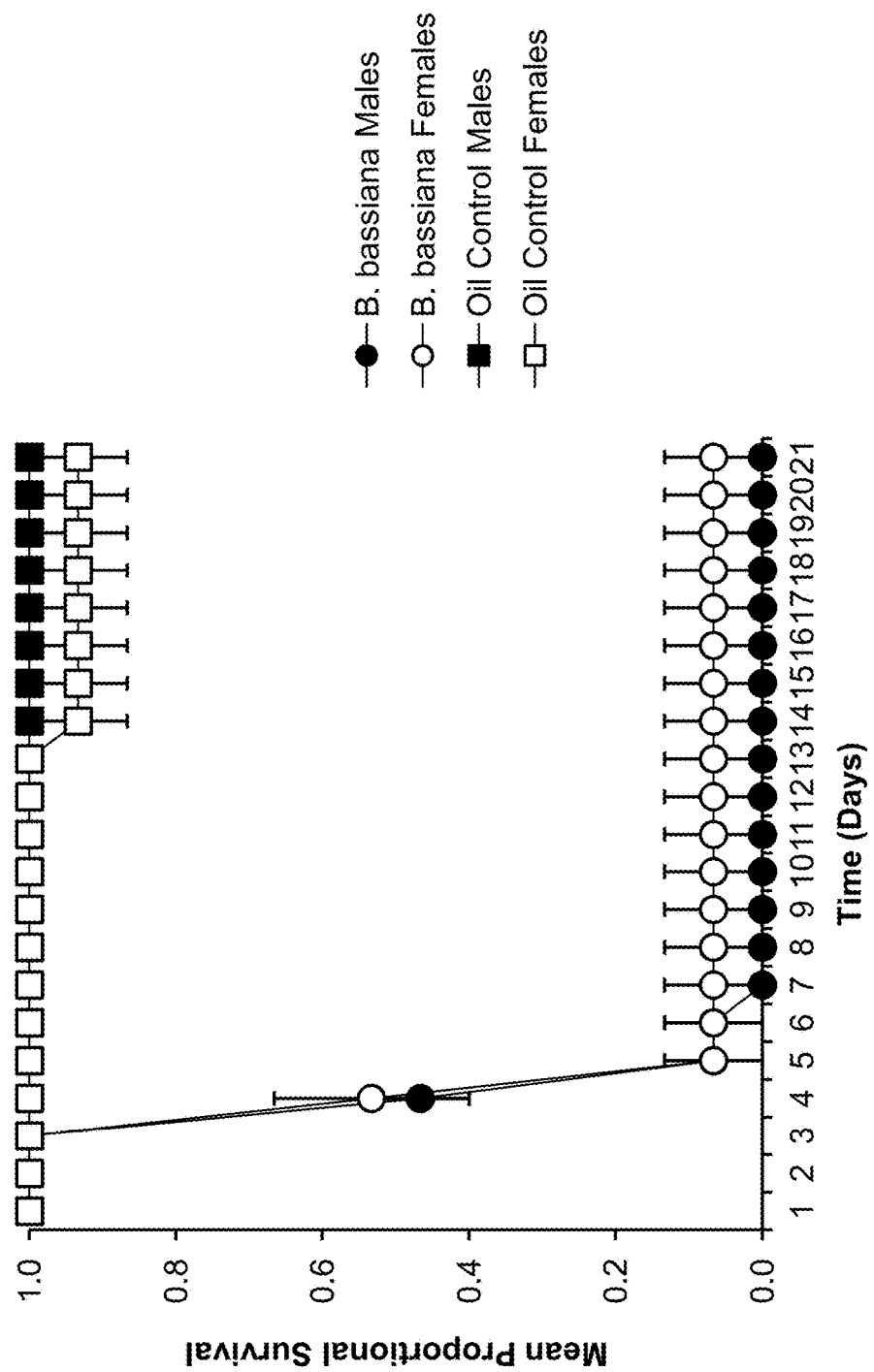
FIG. 2 is a graph showing no difference in bed bug susceptibility between adult male and female bed bugs according to an embodiment of the invention.
Figure 3:
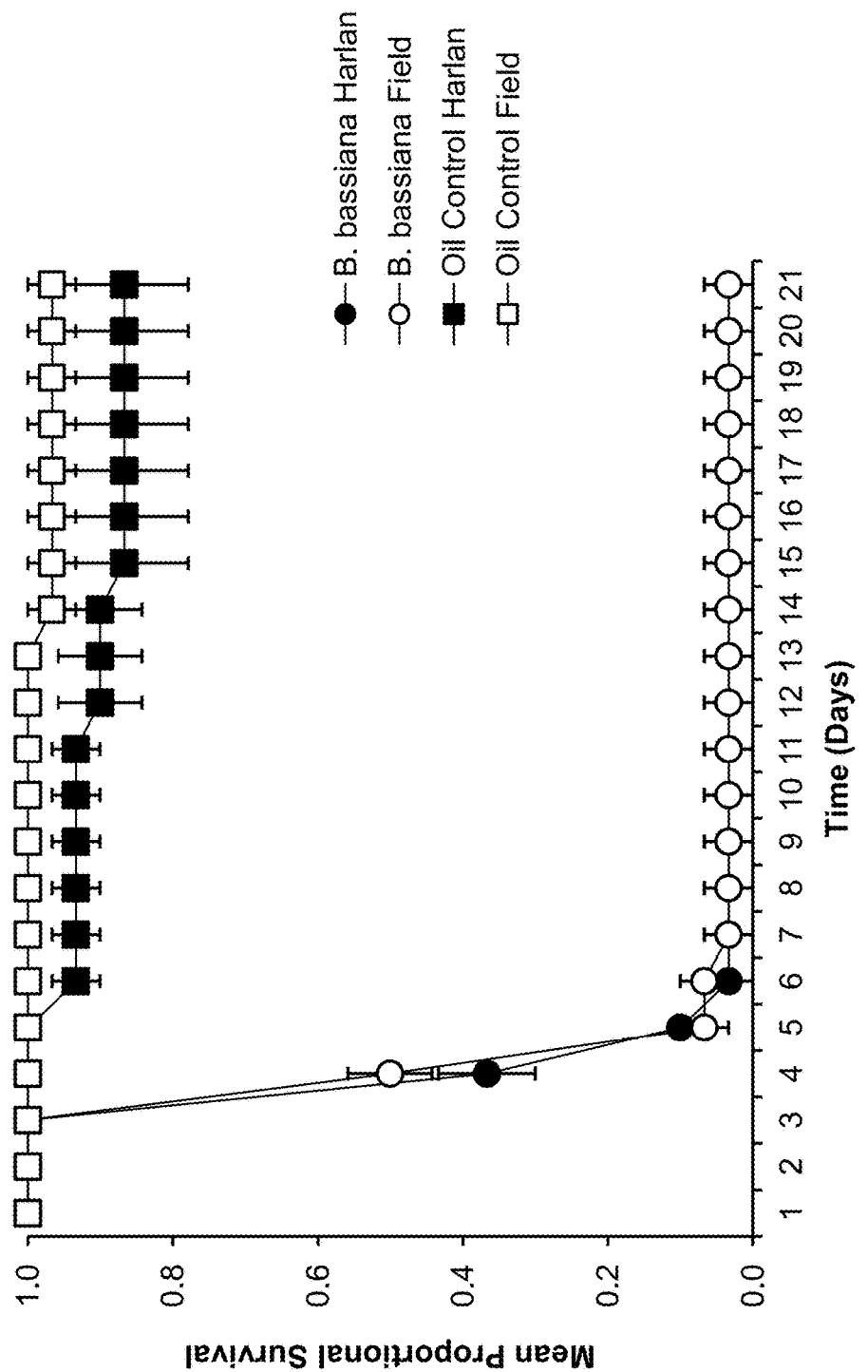
FIG. 3 is a graph showing no difference in bed bug susceptibility due to strain according to an embodiment of the invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to compositions and methods for controlling and/or preventing bed bug populations using entomopathogenic fungi. The compositions and methods of use thereof have many advantages over conventional and existing methods for controlling bed bug populations. For example, the use of certain barrier treatment compositions disclosed in the present invention along with an optional host and/or lure and/or trap ensures the contact of bed bug populations with the entomopathogenic fungi applied to such barrier treatment compositions for eradication of the contacted bed bug and thereafter the horizontal transmission of the entomopathogenic fungi for eradication of additional bed bug populations. The horizontal transmission of the entomopathogenic fungi to additional bed bug populations not directly contacting the barrier treatment composition, provides enhanced control of bed bug populations in harborages, thereby increasing the efficacy of the compositions and methods of the present invention. The present invention represents a significant improvement over the existing means and compositions for controlling bed bug populations as a result of the use of fungal conidia in oil formulations. In addition, the present invention provides suitable compositions and methods for preventing bed bug populations from entering or crossing a particular barrier (e.g. treatment on a suitcase). Such formulations beneficially protect the conidia, allow use at low humidity levels, and increase the pick-up or retention of conidia onto the body of the bed bug for increased efficacy.

The embodiments of this invention are not limited to particular barrier treatment compositions and methods of application or use thereof for controlling and/or preventing bed bug populations, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for example for making concentrates or use solutions in the real world; through inadvertent error in these procedures; through differences in the manufacture, source, or purity of the ingredients used to make the compositions or carry out the methods; and the like. Whether or not modified by the term "about", the claims include equivalents to the quantities.

The term "harborage," as used herein, refers to the locations of a bed bug infestation away from the food source (e.g. blood meal from a human most often in a bed). For example, bed bugs are known to utilize almost every crack or crevice in a home, including headboards, baseboards, dressers, walls, carpet and the like.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the steps, components and ingredients of the present invention as well as other steps, components and ingredients described herein. As used herein, "consisting essentially of" means that the methods and compositions may include additional steps, components or ingredients, but only if the additional steps, components or ingredients do not materially alter the basic and novel characteristics of the claimed methods and compositions.

While an understanding of the mechanism is not necessary to practice the present invention and while the present invention is not limited to any particular mechanism of action, it is contemplated that, in some embodiments, the use of entomopathogenic fungi are well suited for barrier treatments to control bed bug populations. Still further the entomopathogenic fungi are well suited for use in combination with a lure (e.g. human host or an artificial lure), to provide effective control of bed bug infestations. According to a theory of the invention, such methods exploit the natural behavior of bed bug populations, including the behavior of hiding in group harborages that are inaccessible to other control methods. As a result, bed bugs that have been exposed to the entomopathogenic fungi as a result of crossing the barrier treatment compositions to feed on a human host or to investigate an artificial lure, will thereafter serve as vectors for the horizontal transmission of the entomopathogenic fungi to the harborage to further control bed bug populations. As a result a lethal dose of conidia is provided to the harborage (further bed bug population) that would be otherwise inaccessible to traditional chemical methods of eradicating bed bug populations.

Compositions

According to an aspect of the invention a barrier treatment composition is provided. A barrier treatment composition of the present invention is understood to include a variety of substrate surfaces. Substrate surfaces particularly suitable for use in the present invention include those having a texturized surface. Without being limited to a particular theory and/or mechanism of action of the invention, the substrate surface contacted by a bed bug may impact the retention or pick-up of the conidia by the bed bug. Therefore, it is desirable to have a substrate surface that has texture, instead of a flat and smooth surface. In an aspect, the amount of texture a substrate surface is directly correlated to the rate of mortality of the bed bug. For example, a highly textured surface slows down speed of which a bed bug crosses the substrate surface (i.e. increasing contact time) and thereby increases the retention or pick-up of the conidia, correlating to mortality of the bed bug.

The barrier treatment substrates may include the surfaces commonly found in bedrooms, hotels and the like. These include, for example, bed frames, headboards, door and window trim, light switches, baseboards, mattresses, carpet, furniture pieces including for example tables, chairs, dressers and drawers, and the like (which may often include the secondary locations or harborages of bed bug populations), linens, dust ruffles, other bedding and the like. As one of skill in the art will readily ascertain, the barrier treatment compositions can include any of the surfaces of these articles, including for example cracks and crevices of the same wherein bed bugs are expected to traverse. These surfaces can vary in the nature of the substrate, including for example fabrics, wood, laminate, and the like.

In one aspect of the invention a preferred surface for the barrier treatment composition is a fabric. Preferably, the fabric is cotton, such as jersey cotton. Additional surfaces suitable for potential harborages for bed bugs may be suitable for the barrier treatment compositions according to the invention, which may be ascertained by those of ordinary skill in the art and are included in the scope of the present invention. Additional exemplary surfaces would include for example, carpet, cotton towels, polyester microfiber, tape or any manufactured textile onto which conidia could be applied according to the embodiments of the invention.

In a preferred aspect of the invention for use of a fabric prophylactic barrier treatment composition, a fabric surface is employed for covering or otherwise surrounding a point of contact for bed bugs. In an exemplary aspect, a fabric barrier treatment composition is employed as a prophylactic covering for a suitcase or other object which is often a carrier for bed bug populations from an infested location to another. In such an exemplary embodiment, a fabric barrier treatment composition may be employed as a treated cloth bag or covering.

In an alternative aspect, a barrier treatment composition may simply a formulation of the fungal conidia in an oil or oil-based aqueous mixture or suspension that is applied to a fabric or other substrate surface. In an exemplary aspect, the oil or oil-based aqueous mixture or suspension may be directly applied to a suitcase, or other substrate as a spray instead of applying a treated fabric (or other substrate) over such article or surface to protect against bed bug incursion.

The barrier treatment compositions according to the invention are treated with entomopathogenic fungi for providing effective bed bug control and/or prophylaxis measures. Entomopathogenic fungi, as used herein refer to fungi acting as parasites on bed bugs resulting in the death of bed bugs and is further considered a mycopesticide. Entomopathogenic fungi include, without limitation, *Deuteromycetes* and *Hyphomycetes* fungi. Entomopathogenic fungi include, without limitation, the genus *Beauveria, Lecanicillium* (*Verticillium*), *Metarhizium, Paecilomyces, Akanthomyces, Nomurea*, and the like. According to a preferred embodiment, the entomopathogenic fungi are selected from the genera *Beauveria, Lecanicillium* (*Verticillium*), *Metarhizium* or *Paecilomyces*. According to a further preferred embodiment strains of *Beauveria bassiana* are employed as the entomopathogenic fungi for the barrier treatment compositions according to the invention.

Various isolates of *Deuteromycetes* fungi are commercially-available, including for example strain Bb05002 conidia (deposited BRRK 30976 and disclosed in U.S. Pat. No. 8,053,223, which is herein incorporated by reference in its entirety), strains of *Beauveria bassiana* disclosed in U.S. Pat. Nos. 5,683,689, 6,254,864, 6,403,085, and RE38,958, each of where are herein incorporated by reference in their entirety. These exemplary entomopathogenic fungi, and others disclosed herein, lend themselves to use in the barrier treatment compositions of the present invention as biopesticides because, like many conventional chemical insecticide active ingredients, they act through contact. The various fungal species, such as for example, *Beauveria bassiana* and *Metarhizium anisopliae* are capable of infecting a broad range of insect hosts, including bed bugs.

A range of individual isolates of entomopathogenic fungi from the exemplary genus listed above can be screened for virulence to bed bugs by one of ordinary skill in the art. Such screening is suitable for identifying additional isolates, including additional species of entomopathogenic fungi suitable for use according to the invention. An exemplary and non-limiting suitable bioassay technique for such screening would be to formulate conidia of the candidate fungal isolates in mineral oil and spray a surface with a known volume and concentration. The substrate should be dried at room temperature for about 24 hours before allowing a population of bed bugs (of any life stage or feeding status) to the surface for about 1 hour. Following exposure, the bed bugs should be monitored daily for mortality for a period of about 21 days. Alternatively bed bugs could be dipped in an aqueous suspension of conidia or sprayed directly with a known concentration. In all examples, mortality should be monitored daily and compared with a control population. In such a screening program it would be expected that different fungal isolates of the same genus will vary in their pathogenicity/virulence to bed bugs (i.e. resulting in anything from 0% to 100% mortality in about 21 days).

In a preferred aspect, the entomopathogenic fungi are employed in the form of microscopic spores referred to as conidia. As referred to herein, conidia refers to asexual spores of entomopathogenic fungi. For application according to the methods of the present invention, the fungal spores or conidia are further capable of germinating and colonizing the bed bugs causing the fungus to proliferate in the bed bugs' body cavity, resulting in the death of the bed bug. For example, in an aspect of the invention, *Beauveria bassiana* conidia are spherical conidia that form dense bunches of conidiophores. The use of conidia, instead of pre-sporulation entomopathogenic fungi, is beneficial for treatment of the substrate surfaces of the barrier treatment compositions due to the ability to directly apply the conidia without having to wait for sporulation of the fungi and/or providing nutrients/substrates for the sporulation (e.g. common practice for treating insects in soils or other moist environments).

In one aspect of the invention, fungal conidia are formulated in oil for use in the barrier treatment compositions. In an aspect, the fungal conidia are formulated in an oil-based composition, wherein the weight-percentage of oil is at least about 0.1 wt-% or greater, preferably at least about 1 wt-% or greater, and more preferably at least about 10 wt-% or greater. One skilled in the art will ascertain that varying proportions of oil may be used in combination with other oils (e.g. viscous oil with an evaporative oil) and/or with aqueous solutions, which is further included within the scope of the invention using an oil delivery mechanism for the fungal conidia. For example, oil and water mixtures may be employed according to an aspect of the invention. In an aspect, the oil formulation for the fungal conidia is an oil based, water miscible formulation. The various oil-based formulations may include the addition of an aqueous solvent and/or water prior to an application of use. For example, composition comprising fungal conidia may be provided as a powder with components that allow suspension in water and/or as oil concentrates which may further include emulsifiers allowing dilution of the compositions into water.

In an aspect, from about 0.1 wt-% to about 100 wt-% of a viscous oil is formulated for the delivery of the fungal conidia, preferably from about 1 wt-% to about 50 wt-% viscous oil, and more preferably from about 1 wt-% to about 30 wt-% viscous oil. An example of a viscous oil suitable for use according to the invention is Ondina 22 (available from Shell).

In another aspect, from about 0.1 wt-% to about 100 wt-% of an evaporative oil is formulated for the delivery of the fungal conidia, preferably from about 10 wt-% to about 95 wt-% evaporative oil, and more preferably from about 25 wt-% to about 80 wt-% evaporative oil. An example of an evaporative oil suitable for use according to the invention is Isopar M (available from Exxon Mobil).

In a further aspect, the various oil formulations may further employ an optional emulsifier and/or additional functional ingredients for improved stability and/or delivery of the oil formulations. In a still further aspect, the oil formulations for the fungal conidia may be further combined with a wax-based carrier, such as that commercially available as ENTOSTAT powder. In an alternative embodiment, a wax-based powder carrier may be employed for methods of treating bed bug populations according to the present invention (without the inclusion of an oil formulation).

Without being limited to a particular theory or mechanism of action of the present invention, it is believed that the anatomy of the legs of a bed bug are particularly suited for the contact and pickup of conidia formulated in oil. Beneficially, the use of the oil formulations provides a significant increase in the retention or pick-up of conidia spores on the bed bug after contacting the barrier treatment composition in comparison to the retention or pick-up of insecticide particles on a surface from a residual liquid or aerosol insecticide spray treatments. The delivery of the fungal conidia in oil provides further benefits as a result of the increased sticking or adherence of the conidia to the body of the beg bug due to the increased viscosity of the substance, which is significantly increased over conventional insecticide treatments.

In an aspect of the invention the conidia formulated in oil are preferably non-visible (i.e. clear) once applied to the substrate surface. In another aspect, the conidia formulated in oil are odorless. In a still further aspect, the conidia formulated in oil are both clear (non-visible) and odorless.

The treatment of a barrier treatment composition or a substrate surface and/or article with the viable conidia may include coating a surface by any means known to one of ordinary skill in the art with a spore suspension, such as airbrush spraying. A surface may alternatively be soaked, wiped, sprayed with chemical spray equipment, sprayed with domestic and/or industrial spraying devices, or painted onto a substrate surface to apply a suitable concentration of a spore suspension. Preferably the application of viable conidia to a substrate surface results in the even distribution of conidia across the substrate surface from an inoculum of viable conidia.

According to the invention suitable concentrations of spore suspensions for treatment of a barrier treatment composition include at least about 100 conidia per $cm^2$. According to further aspects of the invention, suitable concentrations of spore suspensions for treatment of a barrier treatment composition include about $3\times10^3$ conidia/$cm^2$ to about $3\times10^{10}$ conidia/$cm^2$, preferably from about $3\times10^4$ conidia/$cm^2$ to about $3\times10^8$ conidia/$cm^2$, more preferably about $3\times10^6$ conidia/$cm^2$ (about 20 mL/$m^2$ of $1\times10^9$ conidia/ml). The particular substrate surface (namely amount of texture on the surface) will impact the preferred concentration of the spore suspensions for treatment of a barrier treatment composition. As one skilled in the art will ascertain based upon the disclosure of the present invention, the higher the concentration of the fungal conidia on a barrier treatment will result in a faster rate of kill of bed bugs. In an aspect of the invention, the treatment barrier composition retains a potency of the entomopathogenic fungi for up to at least 3 months. In a further aspect the treatment barrier composition retains a potency of the entomopathogenic fungi for up to at least 4 months, more preferably for up to at least 6 months.

Beneficially, entomopathogenic fungi have low mammalian toxicity allowing the barrier treatment composition to safely come into contact with humans and/or other animals. In addition, the entomopathogenic fungi are considered to be environmentally safe. An additionally beneficial aspect of the invention includes the lack of resistance to fungal biopesticides, including the entomopathogenic fungi of the present invention. Without being limited to a particular theory of the invention, bed bugs have not demonstrated any development of resistance to fungal biopesticides, including any entomopathogens. These are significant advantages over the use of conventional chemical pesiticides, resulting in bed bug resistance and presenting difficulties with respect to human and environmental safety concerns.

The barrier treatment compositions according to the invention may further include a lure. As one skilled in the art will ascertain a lure may include any means for enticing bed bugs to cross the barrier treatment compositions and contact the viable conidia. Lures suitable for the present invention may include both non-artificial and artificial lures. A non-artificial lure may include for example a source of blood, such as a human body for the bed bug to feed on. An artificial lure may include for example, a heat source, a carbon dioxide source, a pheromone or other attractant, octenol and lactic acid and/or a combination of butyric and valeric acids, or combinations of any of such exemplary lures. Still further artificial lures may be embodied according to the invention as one of skill in the art will ascertain based upon the beneficial disclosure of the present invention.

The barrier treatment compositions according to the invention may further include or in the alternative to a barrier treatment, may include a trap. As one skilled in the art will ascertain a trap may include any means for containing bed bugs within a receptacle or other housing instead of allowing a bed bug (or population thereof) to pass across a surface. In an aspect, a tray may contain a barrier treatment composition as described according to the invention herein. In an aspect, a trap may include a barrier treatment composition such that bed bugs enter into a trap and are exposed for an extended period of time the fungal conidia and thereafter upon exiting the bed bugs spread the conidia spores to other bed bug populations.

Beneficially, the barrier treatment compositions according to the invention obviate the need for traditional insecticides or pesticides to be applied to cracks and/or crevices of potential access points of bed bug harborages. In one aspect, the barrier treatment compositions replace the use of botanical insecticides containing natural pyrethrins. This is beneficial, as the control of bed bugs through traditional insecticides or pesticides by either direct hit of spray applications and/or the residual contact of sprayed surfaces does not provide adequate treatment for bed bug populations.

The barrier treatment compositions of the invention have the additional benefits of not damaging the finishes on or the substrate surface itself, such as the damage traditionally caused from the use of petroleum carriers contained in aerosol pyrethrins and/or the undesirable film resulting from the use of inorganic materials such as silica gel, boric acid, and diatomaceous earth.

A still further benefit of the barrier treatment compositions according to the invention is the decreased reliance on pyrethroid insecticides such as deltamethrin, lambda-cyhalothrin and others, as well as other pesticides (e.g. DDT) which have begun to result in bed bug resistance/tolerance.

Methods of Use

In an aspect of the invention, the methods may include, comprise, consist of or consist essentially of providing a barrier treatment composition (or applying a barrier treatment composition for use), delivering viable conidia directly to a bed bug or population of bed bugs, contacting the bed bug(s) and the viable conidia, causing the horizontal transmission of the entomopathogenic fungi to the harborage, and killing a population of bed bugs. The methods may optionally include providing a lure with the barrier treatment composition (non-artificial or artificial). The methods may still further optionally include providing a trap with or without a lure (such trap may further contain the barrier treatment compositions housing the fungal spores according to the invention), such that such beg bugs entering the trap then exit and continue to spread the spores to additional populations of bed bugs (e.g. in a harborage). The methods according to the invention are suitable for use in controlling the population of bed bugs and/or for preventing incursion of a population of bed bugs (e.g. prophylaxis, such as treatment of a room (e.g. hotels, homes) and/or articles commonly contacted by bed bugs (e.g. luggage as a traveler protection system).

As referred to herein, bed bugs are understood to include the family Cimicidae, which includes the human bed bugs *Cimex lectularius, Cimex adjunctus* and *Cimex hemipterus*. The methods and compositions of the invention are effective regardless of bed bug sex (i.e. mixed populations), feeding status and/or strain. In addition, all stages of bed bugs, from nymph to adults ($5^{th}$ instars to $1^{st}$ instars, as bed bugs undergo five immature stages prior to developing into a fully-grown adult) are killed according to the methods of the invention.

According to an aspect of the invention a barrier treatment composition is provided. The providing of the barrier treatment composition may initially employ the step of producing conidia. As one of ordinary skill in the art will ascertain an initial step of producing conidia may be included in the methods of the present invention. A skilled artisan is readily apparent of the various manufacturing processes for producing conidia, such as the procedures used by biocontrol manufacturers to produce virulent spores (Ravensburg, A Roadmap to the Successful Development and Commercialization of Microbial Pest Control Products for the Control of Arthropods. Springer, Dordrecht (2011); Jenkins and Grzywacz, Towards the Standardization of Quality Control of Fungal and Viral Biocontrol Agents. In: Quality Control and Production of Biological Control Agents: Theory and Testing Procedures (J. C. Lenteren, Ed.) p 247-263. CAB International, Wallingford, UK (2003)). Alternatively an inoculated source of conidia may be commercially obtained for the application to the substrate surface. In one aspect of the invention conidia are formulated in oil. Additional description of suitable methods for formulating conidia in oil and compositions of the same are disclosed in Patent GB 2 255 018 (Application No. 9108936.7, filed Apr. 26, 1991), which is herein incorporated by reference in its entirety.

The providing of the barrier treatment composition may also initially include the step of applying or coating a substrate surface with the entomopathogenic fungi compositions (e.g. entomopathogenic fungi in oil and/or oil-based delivery systems). The application of the entomopathogenic fungi compositions provides a barrier treatment, such that the entomopathogenic fungi compositions are positioned between harborages and the human host where the bed bug populations are known to travel for blood meals. The providing of this barrier composition between the harborage and the blood meal ensures the bed bug populations will traverse the barrier (while contacting spores) as they move to and from the host. In an alternative aspect, the barrier treatment (e.g. treatment of a suitcase or other surface/article as prophylaxis) covers a surface/article with the entomopathogenic fungi compositions to prevent bed bugs from entering into such surface/article and/or ensuring the kill of such bed bugs that are able to enter.

The application or coating step may include any means of application known to those skilled in the art. For example, the substrate surface may be coated using by a variety of applying, spraying and/or coating mechanisms, such as using a pressurized tank or other application gun or spraying device, or an airless pump or paintbrush. Alternatively, the entomopathogenic fungi compositions may be manually applied onto a substrate surface in need of treatment, such as applied with a brush, roller or other device for applying a coating of the entomopathogenic fungi compositions. In a still further embodiment, the entomopathogenic fungi compositions may be formulated into a pre-soaked composition (e.g. fabric covering) which is then applied over a surface/article (e.g. a fabric to surround or enclose a suitcase or other article which can often be a means of transporting bed bugs from an infested site to another). Such application steps are not limited to the patterns, thickness, shape, etc. of application. These and other modifications of the particular application are understood by skilled artisans to be dictated by the particular application of use, which are included within the scope of the invention.

The providing of a barrier treatment composition delivers the particular entomopathogenic fungi into the bed bug's environment and/or provides a barrier to prevent bed bugs from entering into another environment (e.g. suitcase). The barrier treatments may comprise, consist of or consist essentially of the compositions disclosed herein. In an aspect of the invention, the providing of a barrier treatment exploits the natural behavior of bed bugs, including the behavior of hiding in group harborages that are inaccessible to other control methods. In one aspect of the invention, a barrier treatment composition may include a substrate treated with the entomopathogenic fungi, such as a bed skirt.

The method of providing a barrier treatment composition must ensure the delivery of conidia directly onto the bed bug. Preferably, providing a barrier treatment composition delivers a lethal dose of conidia directly onto the body of a bed bug. Without being limited to a particular theory of the invention and/or a mechanism of action, it is believed that particular compositions of an entomopathogenic fungi in an oil carrier or oil-based composition beneficially allow the attachment of the fungal conidia to the bed bug in order to allow penetration and infection of the bed bug. (Ulrich, Role of the Bed Bug (Hemiptera: Cimicidae) Cuticle in Attachment and Germination of Entomopathogenic Fungi, Entomological Society of America, Annual Meeting, Nov. 12, 2012). In one aspect, the contact between the bed bug and the conidia in the oil formulations of the barrier treatment compositions, allows for the attachment of the conidia to the cuticle of the bed bug, overcoming delivery limitations identified by Ulrich (2012) (i.e. failure of conidia of *Metarhizium* to stick to the bed bug cuticle, resulting in low infection). Accordingly, the barrier treatment compositions comprising oil formulations of conidia from the entomopathogenic fungi provide conditions suitable for attachment of the conidia to the body of bed bugs. In a further aspect, the oil formulations of conidia further facilitate the carriage of conidia on the body of the bed bug to the harborage where contact with other bugs results in the transfer of conidia.

The methods of controlling bed bug populations further include the additional step of transferring conidia from the body of a bed bug in contact with the barrier treatment composition to additional bed bugs within a harborage. Beneficially, the methods of providing viable conidia to a bed bug allow for the horizontal transmission of the conidia into the bed bugs' environment for its transfer to additional bed bugs therein. The providing of viable conidia directly to bed bugs ensures the viable conidia attached to the bed bugs and allow for horizontal transmission within harborages after the nightly excursions of the bed bugs in search of a blood meal. As referred to herein, "horizontal transmission" refers to the use of bed bugs directly contacting the barrier treatment composition as vectors for further delivering the conidia spores to a second population of bed bugs, such as those within a harborage. Preferably, the horizontal transmission of the conidia provides a lethal dose of conidia to bed bug populations within a harborage, including all stages of bed bugs from $1^{st}$ instar to adults. In a further preferred aspect, the horizontal transmission of the conidia further promotes the eradication of bed bug populations due to the transmission of conidia between mating bed bugs, wherein tissue damage of the bugs caused by traumatic insemination allows for improved transmission and/or infectivity of the conidia.

The methods of the invention further include the contacting of the barrier treatment by the bed bugs in order to expose the bed bugs to the entomopathogenic fungi. In one aspect, a population of bed bugs crosses the barrier treatment and comes into contact with the entomopathogenic fungi as a result of crossing the barrier treatment in an effort to feed on a human host or to investigate an artificial lure. According to the invention, the bed bugs having contacted the entomopathogenic fungi thereafter serve as a vector for the horizontal transmission of the entomopathogenic fungi to the harborage. In an aspect the bed bugs provide the horizontal transmission of a lethal dose of the entomopathogenic fungi, such as conidia, back to the harborage. As one skilled in the art will ascertain, the horizontal transmission of the entomopathogenic fungi can include delivery to any harborage of the bed bugs, including for example, behind base boards, electrical plates and other areas that are otherwise inaccessible except by means of such horizontal transmission. Such horizontal transmission overcomes a significant limitation of known pesticide or insecticide treatments wherein there is little to no residual pick-up of the chemicals onto the bed bugs for such horizontal transmission. Accordingly, the biopesticide compositions of the present invention beneficially result in both significant residual exposure and horizontal transmission to bed bug harborages.

Alternatively, the methods of the invention may provide a direct source of an entomopathogenic fungi sprayed onto a surface. In one aspect, conidia may be sprayed directly to a surface to infect bed bugs on the surface. In another aspect, conidia may be sprayed directly to a surface to infect bed bugs subsequently contacting the spray residue.

The methods of the use according to the invention exploit the highly gregarious habits of the bed bugs, where all life stages aggregate in harborages. This behavior greatly increases the potential for horizontal transmission and secondary cycling of diseases within a population, providing previously unachieved success in controlling bed bug populations. The impact of pathogen cycling is significant within the methods of the present invention. According to the invention the spreading of the conidia or other entomopathogenic fungi extends to inaccessible areas frequented by bed bugs, providing superior results over conventional chemical control measures.

The methods of the invention and employing the barrier treatment compositions of the invention are suitable for use at a wide range of temperatures. In one aspect, the invention is suitable for use in the ranges of about 0 C to about 60 C, from about 10 C to about 40 C, preferably about 15 C to about 34 C, and most preferably from about 20 C to about 28 C.

According to the invention, the population of bed bugs crossing the barrier treatment of the invention will result in a contact kill within about 24 hours to less than about 10 days. Preferably the contact kills as a result of the entomopathogenic fungi results within about 24 hours to 9 days. The contact kill resulting from the horizontal transmission of the entomopathogenic fungi results within about 10 days, preferably within about less than 6 days, less than about 5 days, less than about 4 days, or still more preferably within 3 days. As a result there are benefits of the methods of the invention over the various commercially-available materials for bed bug control, including for example Phantom® (chlorfenapyr) which generally requires at least ten days for a 50% kill of a test population kill (and still longer for complete eradication of a bed bug population), during which time the bed bug populations remain active and deposit viable eggs in other locations.

Following an application of conidia according to the invention (e.g. spray application), conidia remain viable for about 3 or more months at room temperature, thus effecting control on all bed bugs that contact the sprayed surface. According to a further embodiment of the invention, conidia remain viable for more than 3 months at room temperature to provide residual or continued control on all bed bugs that contact the sprayed surface, preferably more than 6 months at room temperature providing a prophylactic option for controlling bed bug populations.

In addition to the residual efficacy of the conidia on the treated barrier surface composition (e.g. efficacy as a prophylactic regimen), the methods of the invention are further efficacious for bed bug control as a result of the horizontal transmission to unexposed bed bugs via contact with bed bugs carrying conidia via contact with the spray residue. Secondary cycling of the fungal disease via liberation of conidia from the cadavers of fungus killed individuals, particularly in harborages, is an additional mechanism of bed bug control efficacy according to the invention. According to the various mechanisms of action of the present invention, the bed bug control efficacy as a result of the methods and compositions of the invention can continue for a period of months to years.

In an aspect of the invention, the methods result in a complete (e.g. about 100%) kill of a bed bug population. In another aspect the methods result in up to at least about 95% kill, up to at least about 90% kill, up to at least about 85% kill, up to at least about 80% kill, up to at least about 75% kill, or up to at least about 70% kill. In another aspect of the invention, the methods of providing the entomopathogenic fungi biopesticide result in the control of bed bugs without the development of resistance or tolerance towards the entomopathogenic fungi. In a still further aspect, the methods of the invention provide enhanced control of bed bugs in comparison to the use of botanical insecticides such as natural or synthetic pyrethrins.

In certain aspects of the invention, the methods of using the barrier treatment compositions provide prophylactic treatment of surfaces for prevention of bed bug infestations. In an aspect, the barrier treatment compositions are routinely applied to surfaces commonly trafficked by bed bugs, such as every 3 to 9 months, or every 4 to 6 months, or some other frequency. The maintained viability of the conidia of the barrier treatment compositions allows the use of the biopesticides for prophylactic application to surfaces where bed bugs would be expected to traverse.

The residual efficacy of the oil formulations allowing horizontal transmission of the conidia provides a further benefit for prophylactic treatments. In an aspect, it is understood that bed bug infestations are challenging due to difficulty in identifying and targeting all concealed harborages of bed bug populations. However, due to the nightly excursions from harborages in search of a blood meal by the bed bugs, the residual efficacy of the conidia in the barrier treatment compositions provides a constant control against bed bug populations.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

A series of bioassays were conducted on the human bed bug *Cimex lectularius*, to evaluate the efficacy of *Beauveria bassiana* as a residual biopesticide treatment. Populations of bed bugs were obtained and reared along with fungal isolates harvested for the subsequent testing of the efficacy of *B. bassiana* as a biopesticide against common bed bugs of various feeding statuses, sexes, strains, exposure substrates, and three life history stages.

Bed Bugs

A pesticide-susceptible laboratory strain of bed bugs was obtained and designated "HS" strain. The strain was originally established by Harold Harlan (National Pest Management Association, Fairfax, Va., USA) from a population collected in Fort Dix, N.J., USA in 1973 and has been reared in the laboratory exclusively since that time. A second strain was obtained and designated "FS". The strain was established by Ecolab® employees in 2005 by combining specimens collected from field infestations in Minnesota, Wisconsin, Florida, and New Jersey.

Both strains were reared under standard conditions of 27±0.5 C, 50±5% relative humidity (RH), and 14:10 (L:D) in glass rearing jars containing folded filter paper (Whatman Nol, 90 mm) for a harborage. Jars were covered with organza fabric with a pore size <1 mm for ventilation. Colony bed bugs were offered a blood meal weekly via an artificial feeding system (Montes et al., 2002). All bed bugs were fed human blood since other blood sources have been known to affect bed bug growth and survival (Barbarin, Unpublished data). Circulating hot water maintained the human blood at 37 C.

Fungal Isolate

*B. bassiana* 193-825 was maintained in long-term storage at −80° C. on microporous beads (Pro-Lab Diagnostics, Austin, Tex., USA). Prior to production, the fungus was recovered by placing one or two beads onto Sabouraud-dextrose agar (Oxoid, UK) in 9 cm diameter Petri dishes and incubated at 25° C. for 10 days.

Conidia were harvested from SDA plates to make a spore suspension of approximately $1 \times 10^6$ conidia $ml^{-1}$ in sterile 0.05% w/v Tween 80 (Sigma) in distilled water. One ml of this suspension was then used to inoculate 75 ml sterile liquid culture medium (4% d-Glucose, 3% yeast extract [Oxoid, UK] in tap water), in 250 ml Erlenmyer flasks. Flasks were incubated on a rotary shaker (160 rpm) at 22±1° C. for 4 days.

Barley flakes (Bobs Red Mill, Milwaukie, Oreg., USA) were weighed into mushroom spawn bags (Unicorn, Garland, Tex., USA), 1 kg per bag and 600 ml tap water was added and the contents mixed by hand to ensure even absorption of the water. The spawn bags were then placed inside autoclave bags for protection and autoclaved for 30 min at 121° C. Once cool the bags were inoculated under aseptic conditions with 75 ml of the 4 day old liquid medium plus 75 ml of sterile water to achieve a final moisture content of approximately 48%. The inoculated bags were carefully massaged to ensure even distribution of the inoculum. The bags were then sealed and incubated on shelves for 10 days at 22±1 C. Following incubation, the bags were opened in a reverse flow cabinet (Labconco, USA) and the contents transferred to brown paper bags for drying. The paper bags were placed in a dehumidified room for 4 days (22±1 C), until the sporulated substrate reached <20% moisture content. The conidia were then harvested from the barley flakes using a Mycoharvester (Acis Manufacturing, Devon, UK).

The harvested conidia were placed in glass dishes and further dried in a desiccator over dry silica gel at 24 C. Once the conidia powder reached 5% moisture content, a small sample was taken for quality analysis (viability, moisture content and contamination—according to Jenkins & Grzywacz, Towards the Standardization of Quality Control of Fungal and Viral Biocontrol Agents. In: Quality Control and Production of Biological Control Agents: Theory and Testing Procedures (J. C. Lenteren, Ed.) p 247-263. CAB International, Wallingford, UK (2000 & 2003)) and the remaining powder was sealed in foil laminated sachets with a small sachet of silica gel and stored at 5 C until use.

Conidia were formulated in oil containing 80% Isopar M (Exxon Mobil) and 20% Ondina 22 (Shell). The formulation was homogenized by vortexing for 30 s and sonicating in a bath sonicator an additional 30 s to break up aggregates of conidia. The concentration of conidia per ml was estimated using an improved Neubauer hemacytomer and adjusted to a concentration of $1.6 \times 10^9$ conidia/ml.

Application of Conidia to Exposure Substrate

Figure 4:
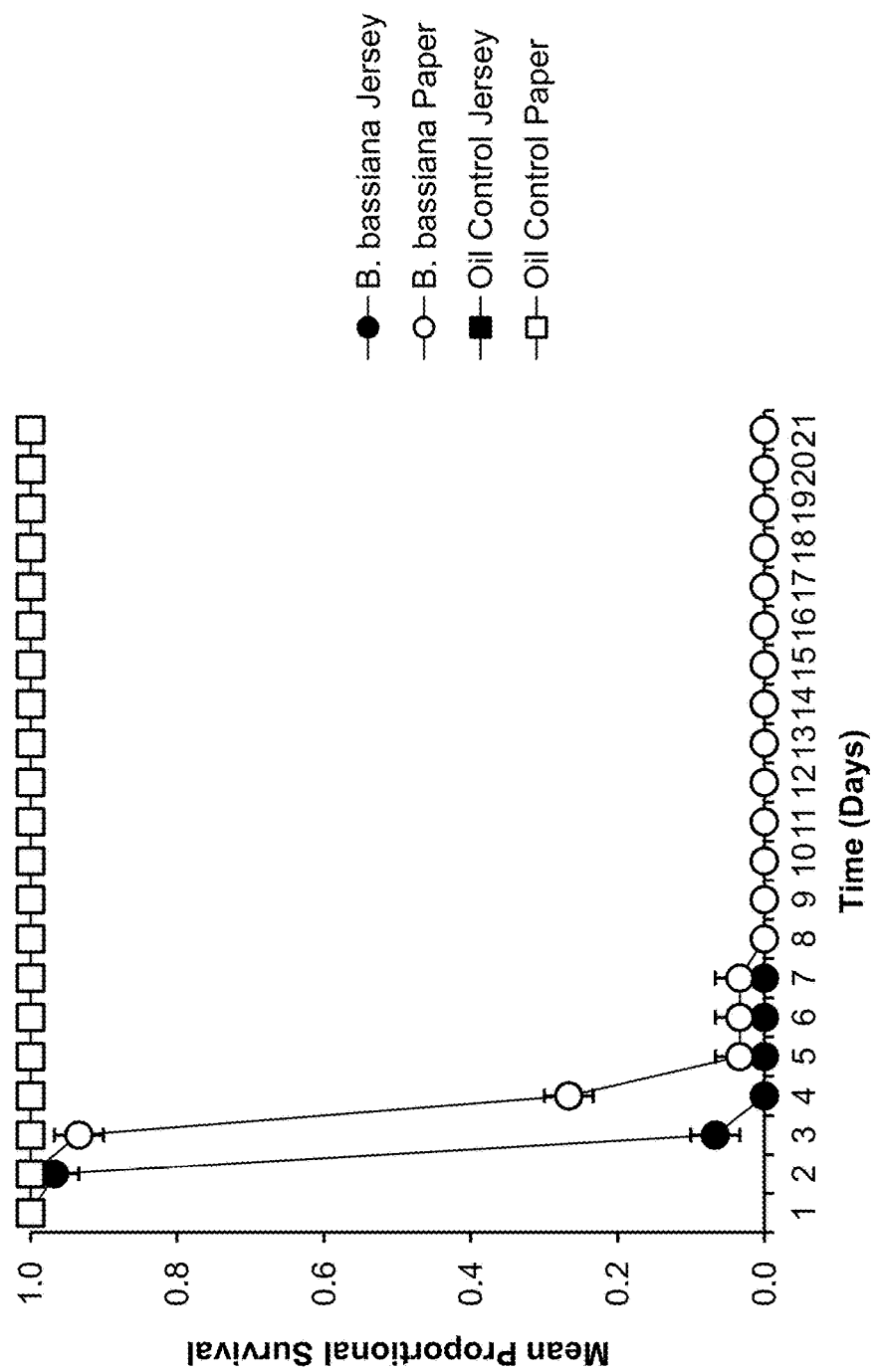
FIG. 4 is a graph showing a difference in bed bug susceptibility due to substrate according to an embodiment of the invention.

Conidial formulations were applied to substrates (paper or cotton jersey) at a rate of $3 \times 10^6$ conidia/$cm^2$ using an airbrush sprayer. The conidial suspension was loaded into the airbrush reservoir and sprayed to give an equivalent volume application rate of 20 mL/$m^2$. The airbrush sprayer was moved by hand at a constant rate and distance from the substrate during the spraying process to ensure even coverage. Spore formulations were applied to HP™ Color-Laser Paper or to 50×50 cm squares of jersey knit cloth, which were then cut into 9 cm circles. Both paper and jersey knit cloth exposure substrates were taped inside a 0.25 $m^2$ spray area on the rear wall of a reverse flow hood. Control substrates were sprayed with blank formulation oil only.

After spraying, substrates were removed from the wall of the hood and allowed to dry at room temperature overnight. Coverage of conidia was verified by cutting three replicate 2 $cm^2$ swatches of the sprayed substrate (paper or cotton jersey) and suspending in a 3 mL of Isopar M. The conidia were extracted from the substrate by vortexing and sonicating as described above. The number of conidia per cm was calculated by counting the resulting conidial suspension using an improved Neubauer heamacytomer.

Exposing Bed Bugs to Fungal Spores

For the bed bug life stage and sex comparisons, bugs of appropriate instar and/or sex were randomly collected from the main colonies. For all other experiments, adults of mixed sex were selected. Bed bugs were removed from the main colony the day prior to experimentation. In all experiments bed bugs were fed 12 hr. prior to experimentation except for those designated "unfed" in the fed versus unfed comparison. After feeding, bed bugs were placed in 30 mL plastic diet cups (Dart, USA).

Three replicates of ten bed bugs were exposed to each treatment. Bed bugs were removed from the diet cups and placed on the pre-sprayed, dry substrate in a Petri dish using feather-weight forceps and allowed to remain in contact with the sprayed substrate for 1 hr. After exposure, bed bugs were placed in a clean Petri dish with clean filter paper on the bottom. Post treatment all bed bugs were fed on days 7, 14, and 21 following exposure.

Monitoring Survival

The number of dead bed bugs in each replicate was recorded daily for 21 days following exposure. Dead bed bugs were not removed from the dishes until the end of the experiments. Mortality data were used to construct survival curves.

Sporulation of Cadavers

To determine fungal sporulation rates, dead bugs were placed in 30 mL diet cups with silica gel and allowed to dry for at least one week to prevent putrefaction due to bacterial growth. After removing the silica gel, cadavers were placed into clean diet cups containing a saturated piece of paper towel and sealed with an airtight lid. The treatment and date of death for each cadaver was noted to determine sporulation rates based on those factors. The cups containing bed bug cadavers were placed into an incubator at 23 C and assessed for fungal growth after 3 to 4 days using a stereomicroscope at 15× magnification. Sporulation was determined by the presence of mycelium and or spores emerging from the intersegmental membranes of the cadaver.

Statistical Analysis

Bed bug survival data were analyzed using Kaplan-Meier survival analysis (SPSS, software version 18). Differences in median survival time between treatments were compared using the log-rank test.

Impact of Feeding Status, Sex, Strain, and Substrate

Test bed bugs of appropriate sex and strain were extracted from the HS and FS main colonies and placed on the appropriate exposure substrate. All were fed 12 hours prior to exposure except for the starvation group that was starved for 14 days prior to exposure. In the sex experiment, three replicates of 10 (five males and five females) for each strain were exposed. All other experiments were conducted with mixed sex bed bugs. The next experiment evaluated the effects of strain; three replicates of 10 bed bugs for each strain (HS and FS) were exposed. All subsequent experiments after the strain comparisons used FS. The third experiment evaluated the impact of substrate type on mortality; three replicates of 10 bed bugs of FS were exposed to fungus-treated paper or jersey knit cotton. All supplementary experiments following the substrate comparison used jersey knit cotton.

Impact of Life History Stage

Bed bugs were removed from the general FS colony and grouped according to instar. Twelve hours prior to substrate exposure, all bed bugs were fed human blood on an artificial feeder. On the day of exposure, bed bugs were placed in groups of ten according to instar, and placed on treated substrate for one hour. After exposure, bed bugs were placed into clean Petri dishes in the same groups of ten according to instar. Bed bugs were monitored daily for mortality, and surviving bugs were fed a blood meal 7 and 14 days following exposure to substrate.

Results

Susceptibility Due to Feeding Status

There was no difference in mean survival times of fed versus unfed bed bugs on paper substrate (chi-square=1.507, d.f.=1, p=0.220) (FIG. 1). The mean survival of fed and unfed bed bugs was 3.667±0.118 days and 3.466±0.158 days, respectively. Additionally, 100% of all fed and unfed bed bug cadavers sporulated. As shown in FIG. 1, Mean proportional survival of bed bugs, exposed to paper sprayed with oil formulation of *B. bassiana* conidia resulting in 3×106 conidia/cm2 (circles) or blank oil formulation (squares) for 1 hour. Bed bugs were either blood fed 12 h prior to exposure (black circles) or left unfed prior to exposure (grey circles). Data points represent the mean (+/−SE) of 3 replicates of 10 bed bugs.

Susceptibility Due to Sex

Mean survival times of adult male and female bed bugs of FS were not different (chi-square=0.328, d.f.=1, p=0.567) (FIG. 2). Mean survival time after exposure to sprayed paper substrate was 4.6±0.214 days and 5.6±1.070 days for males and females, respectively. Total control mortality was less than 10%. Again, sporulation of all treated males and females was 100%. As shown in FIG. 2, mean proportional survival of fed male (black circles) and fed female (grey circles) bed bugs, exposed for 1 h to paper sprayed with oil formulation of *B. bassiana* conidia resulting in 3×106 conidia/cm2 (circles) or control blank oil formulation (squares). Data points represent the mean (+/−SE) of 3 replicates of 10 bed bugs.

Susceptibility Due to Strain

Mean survival times of adult HS and FS bed bugs were not different (chi-square=0.259, d.f.=1, p=0.611) (FIG. 3). The mean survival time of HS bed bugs was 5.033±0.559 days; mean survival time of Field Strain bed bugs was 5.1±0.552 days. Total control mortality was less than 10%. The sporulation of all bed bug cadavers of treated Harlan and Field Strains was 100%. As shown in FIG. 3, mean proportional survival of fed Harlan strain (black circles) and ECL-05 strain (grey circles) bugs, exposed to paper sprayed with oil formulation of *B. bassiana* conidia resulting in 3×106 conidia/cm2 (circles) or control blank oil formulation (squares) for 1 hour. Data points represent the mean (+/−SE) of 3 replicates of 10 bed bugs.

Susceptibility Due to Substrate

Mean survival times of adult bed bugs were shorter following exposure on sprayed jersey cotton than for adults exposed to sprayed paper (FIG. 4) (chi square=71.021, d.f.=1, p<0.001). Bed bugs exposed to jersey knit substrate had a mean survival time of 2.879±0.055 days compared the mean survival time of bed bugs exposed to paper substrate (4.233±0.139 days). Mortality was 100% in both treatments. Total control mortality was less than 10%. The sporulation rate of bed bugs exposed to both treated jersey knit and paper substrate cadavers was 100%. As shown in FIG. 4, mean proportional survival of fed bed bugs, exposed to paper (grey circles) or cotton jersey (black circles) sprayed with an oil formulation of *B. bassiana* conidia resulting in 3×106 conidia/cm2 or blank oil formulation (squares) for 1 hour. Data points represent the mean (+/−SE) of 3 replicates of 10 bed bugs.

Susceptibility Due to Life Stage

Figure 5:
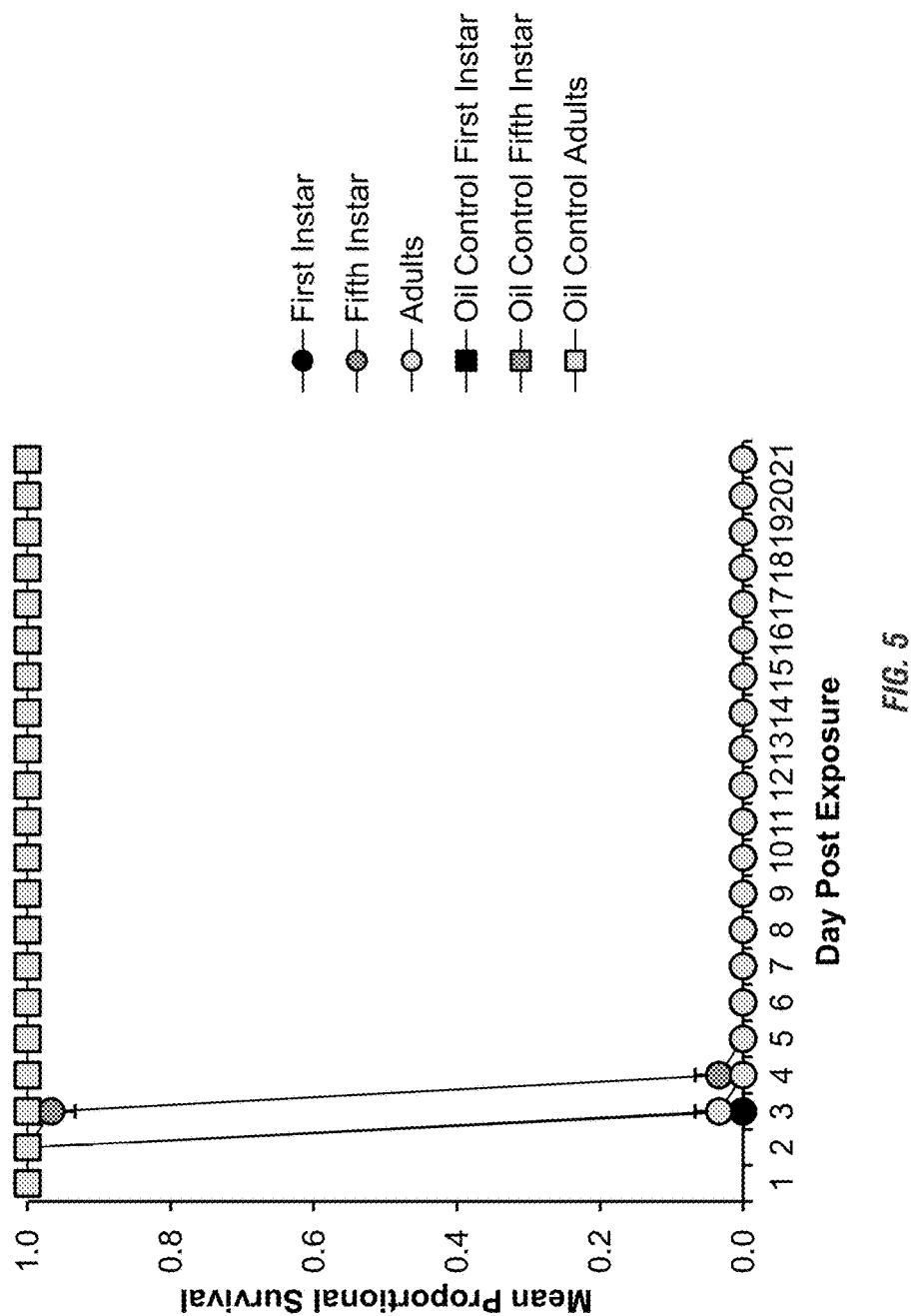
FIG. 5 is a graph showing no difference in bed bug susceptibility to infection due to life stage according to an embodiment of the invention.

All bed bug instars tested were susceptible to infection, following exposure to sprayed jersey material (FIG. 5). Mean survival time for first instar bed bugs was 3.00 days (±0.00 days). The mean survival time of fifth instar bed bugs was 4.00±0.048 days. And the mean survival time of adults was 3.033±0.033 days following exposure to treated jersey knit substrate. When compared to first instars, fifth instar bed bugs survived significantly longer after exposure to jersey knit substrate (chi-square=55.194, d.f.=1, p<0.001). Fifth instar bed bugs also survived significantly longer after exposure to jersey knit substrate than adult bed bugs (chi-square=51.208, d.f.=1, p<0.001). Mortality of first instar and adult bed bugs was not statistically different (chi-square=1.000, d.f.=1, p=0.317). Total control mortality was less than 10%. Sporulation rates of treated cadavers in first and fifth instars, and adult bed bugs were 100%.

As shown in FIG. 5, mean proportional survival of fed first instar (black circles), fifth instar (grey circles) and adult (open circles) bed bugs, exposed to cotton jersey sprayed with an oil formulation of *B. bassiana* conidia resulting in 3×106 conidia/cm2 (circles) or blank oil formulation (squares) for 1 hour. Data points represent the mean (+/−SE) of 3 replicates of 10 bed bugs.

Results

*Beauveria bassiana* (I93-825) was highly virulent, causing rapid mortality following short-term exposure to spray residue. Mortality levels were generally 100% indicating complete susceptibility to fungal infection under these exposure conditions. In a couple of assays 5 to 8% of individuals did not die but re-exposure of these few survivors resulted in infection and mortality (results not shown), suggesting sub-optimal pick up of spores (especially from the paper substrate) rather than any physiological resistance.

With respect to test substrates, Jersey knit cotton provided an improved substrate for conidial transfer in comparison to paper, probably due to the relatively contoured surface resulting in more conidia coming into contact with the insect cuticle. These results demonstrate that choice of substrate is important in both bioassay design and end product development. Studies exploring transfer of conidia to mosquitoes following short-term residual exposure also show substrate type to effect infection levels and spore persistence.

Overall, the results demonstrate efficacy of entomopathogenic fungi on two strains of *Cimex lectularius*. The efficacy of *B. bassiana* was demonstrated on control of bed bugs of different feeding status, sex, strain, on different treatment substrate, and life stage. The *B. bassiana* is very effective against bed bugs in laboratory tests, and quickly kills bed bugs regardless of feeding status, sex, strain, exposure substrate, and life stage.

Example 2

The efficacy of *Metarhizium anisopliae* (strain ESF1 (EPA, 2001)) as a biopesticide against common bed bug in laboratory conditions was evaluated using standard laboratory bioassay, using fed adult bed bugs and identical methods to those described in Example 1.

Figure 6:
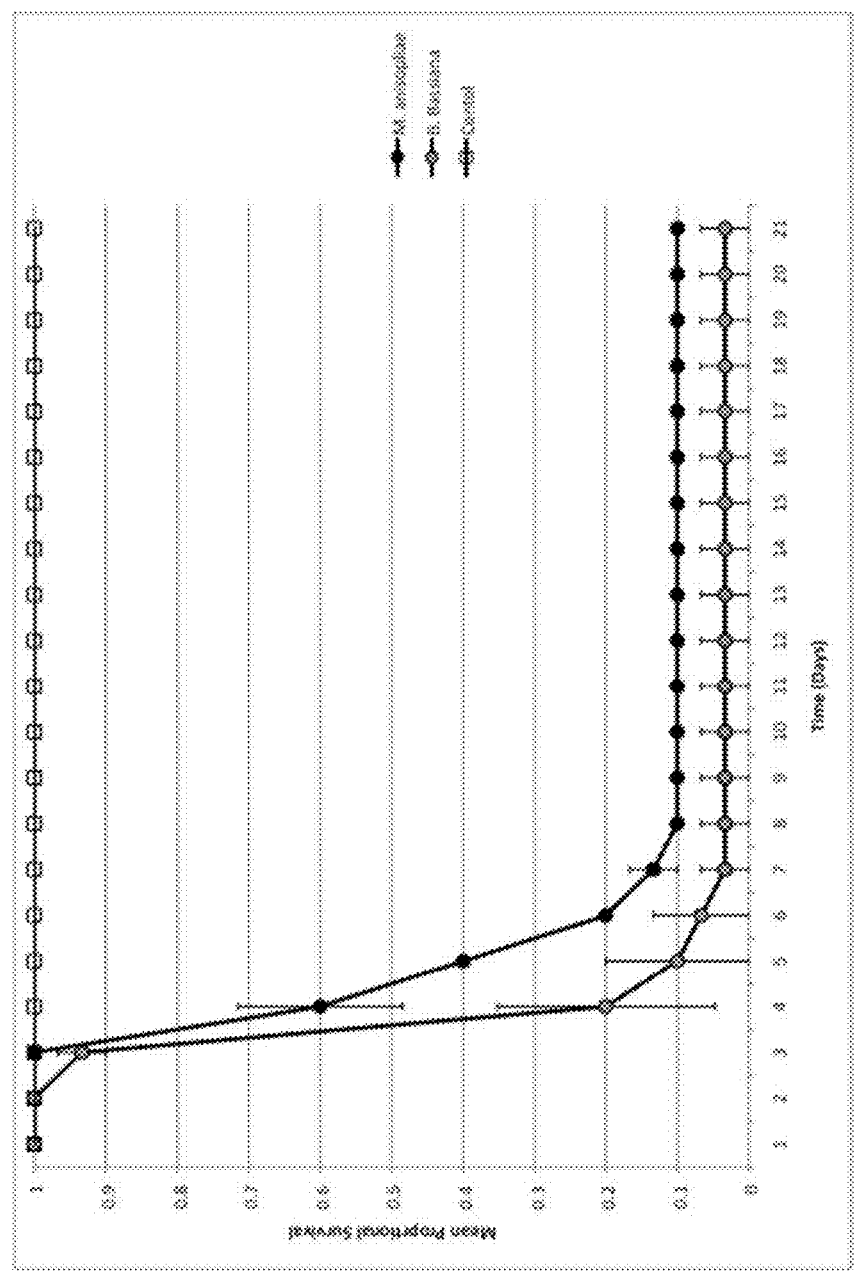
FIG. 6 is a graph showing comparison of bed bug control using varying isolates of entomopathogenic fungi (*M. anisopliae* versus *B. bassiana* versus control) according to an embodiment of the invention.

The results demonstrate efficacy of *M. anisopliae* on *Cimex lectularius*. *M. anisopliae* is effective against bed bugs in laboratory tests, and quickly kills bed bugs with 5 days. FIG. 6 shows the comparison of efficacy of bed bug control using *M. anisopliae* versus *B. bassiana* (and further shown against control as described in Example 2). The graph shows that *B. bassiana* provides superior bed bug control (demonstrated through mean proportional survival), however the isolate *M. anisopliae* also provides bed bug control according to the compositions and methods of the invention.

Example 3

Further analysis demonstrating the efficacy of the horizontal transmission according to the invention was completed. Horizontal transmission of *B. bassiana* conidia following exposure of bed bugs to a sprayed surface (applied at a rate of $3 \times 10^6$ conidia/cm$^2$ using an airbrush sprayer) was conducted according to methods of Example 1 (and as further described herein). One hundred twenty adult, mixed sex bed bugs were removed from the FS colony, fed, and placed into 30 mL diet cups in six groups of 20 and left overnight. The following day, ten bed bugs were removed at random from each group and exposed to either treated jersey cotton or unsprayed jersey cotton (3 replicates each) and allowed to remain in contact with the substrate for 1 hour. After exposure, bed bugs were returned to their respective diet cups (e.g. artificial harborage) to comingle with the 10 "clean" (unexposed) bed bugs. A sterile filter paper harborage was provided, wherein 20 bed bugs were in each artificial harborage—10 exposed, 10 unexposed, three replicates of the same. Mortality of the entire population was assessed daily as above.

Figure 7:
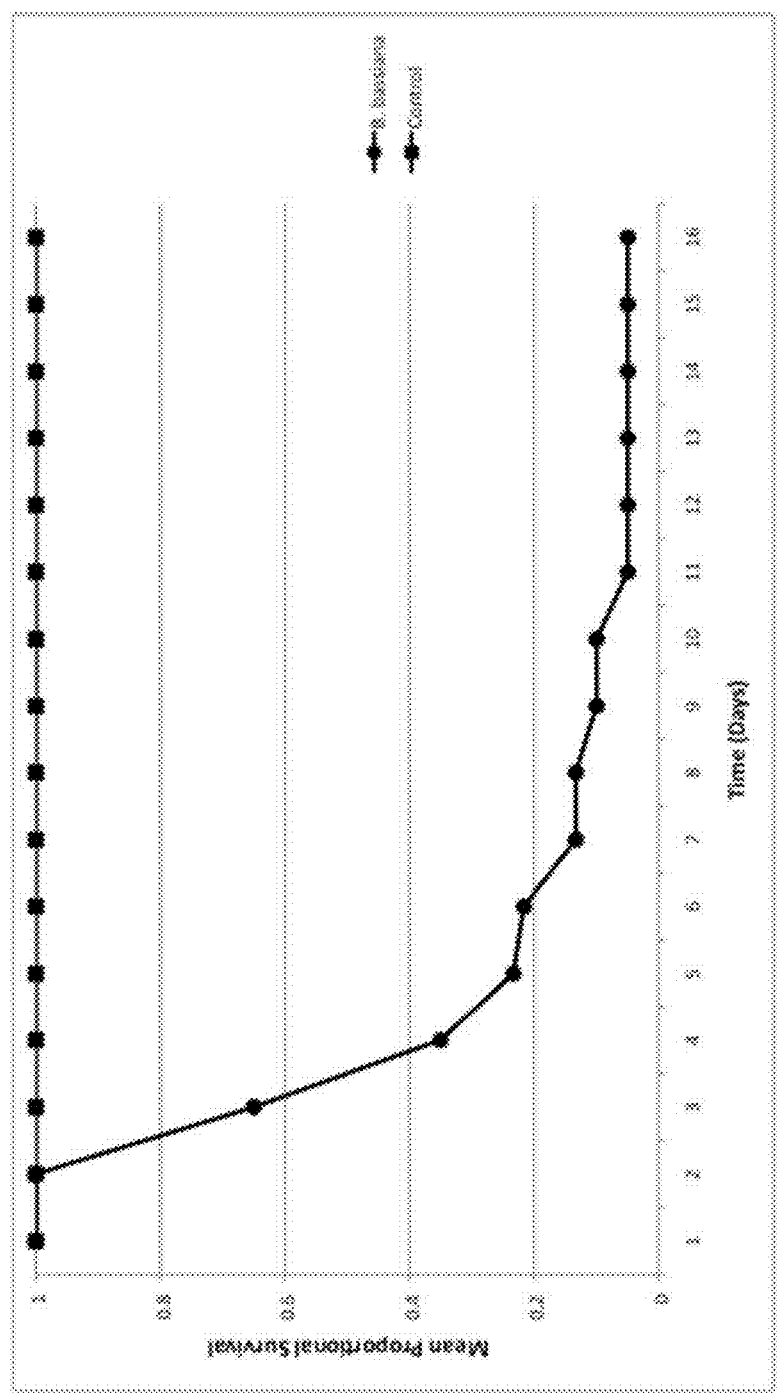
FIG. 7 is a graph showing the proportional survival of entire population of bed bugs following exposure of half the population to a surface treated with *B. bassiana* demonstrating the efficacy of horizontal transmission according to an embodiment of the invention.

As shown in FIG. 7, Mean proportional survival of fed adult bed bugs, exposed to cotton jersey sprayed with an oil formulation of *B. bassiana* conidia resulting in $3 \times 10_6$ conidia/cm$_2$ (black circles) or blank oil formulation (gray squares) for 1 hour. Data points represent the mean (+/−SE) of 3 replicates of 20 bed bugs, (10 exposed and 10 unexposed each).

Horizontal transmission according to the invention is demonstrated as the entire population of 20 bed bugs go on to die of the disease. This confirms that not only the 10 exposed bugs are killed—in addition the 10 unexposed bed bugs are killed as a result of horizontal transmission of the *B. bassiana* conidia. Overall mortality is slightly slower than seen in the directed exposure experiments because the unexposed bed bugs may not acquire the disease immediately after introduction of the exposed bed bugs. FIG. 7 shows the proportional survival of entire population of bed bugs following exposure of half the population to a surface treated with *B. bassiana*. Three replicate treatments containing 10 exposed bed bugs plus 10 unexposed bed bugs. All data pooled in this FIG. 60 bed bugs total).

Example 4

Figure 8:
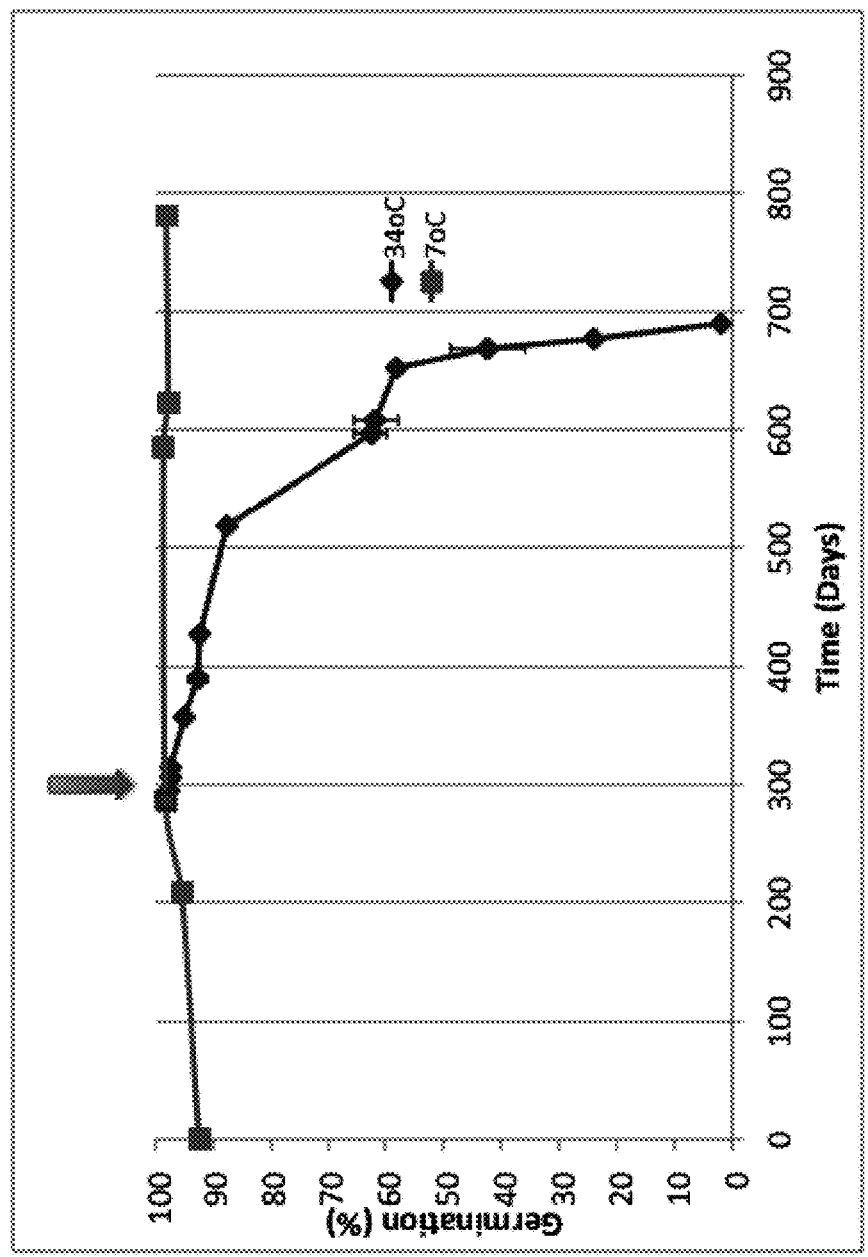
FIG. 8 is a graph depicting the viability and long term shelf-life of *B. bassiana* conidia for periods of up to 800 days according to embodiments of the invention.

The stability and retained efficacy (i.e. shelf life) of the barrier treatment compositions of the invention were evaluated. The persistence of a spray residue applied to a barrier treatment composition (applied at a rate of $3 \times 10^6$ conidia/cm$^2$ using an airbrush sprayer) was analyzed to determine stability for extended periods of time. A *Beauveria* isolate as described according to the invention was analyzed. *Beau-* veria bassiana conidia was harvested from production and dried to 5% moisture content. The conidia were stored in foil laminate sachets at 7 C for 800 days (depicted as squares in FIG. 8) or stored for 300 days at 7 C and then transferred to 34 C for an additional 400 days (depicted as diamonds in FIG. 8). As shown in FIG. 8, the viability of *Beauveria bassiana* conidia store for up to 800 days at 7 C showed no decrease in germination, demonstrating the extended stability of the harvested conidia according to the invention.

Figure 9:
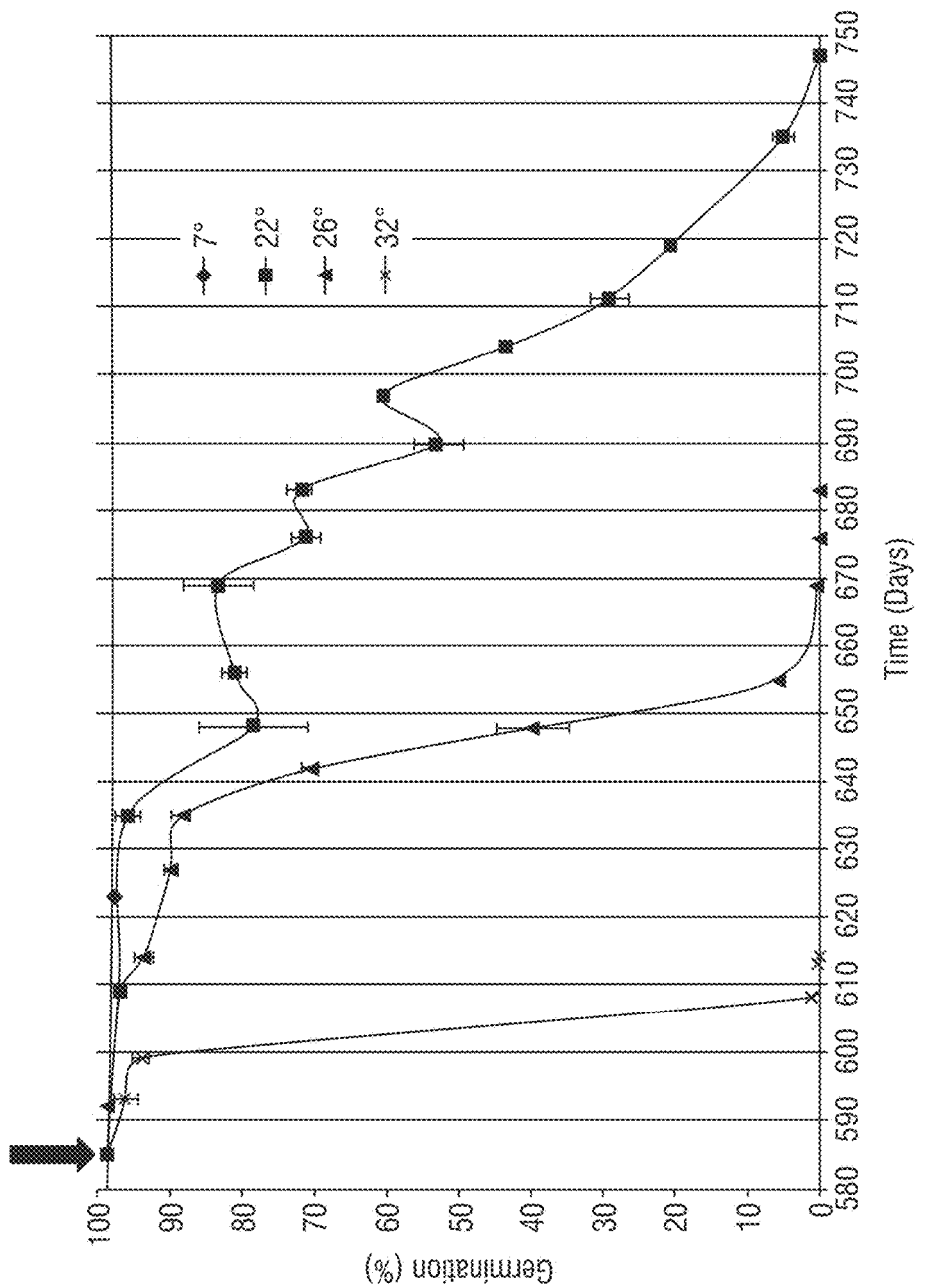
FIG. 9 is a graph showing the survival of unformulated conidia at high humidity-low humidity results in enhanced survival as does oil formulation according to embodiments of the invention.

The stability of *Beauveria bassiana* conidia were also examined to determine long-term storage under varying temperature and humidity conditions. The viability of the *Beauveria bassiana* conidia was evaluated after long-term storage in foil laminate sachets (7 C for 585 days). The conidia sachets were transferred to open containers in environmental chambers with 80% humidity and the following varying temperatures: 22 C (depicted as squares in FIG. 9), 26 C (depicted as triangles in FIG. 9) and 32 C (depicted as "x" in FIG. 9) for up to 160 days. This graph shows the survival of unformulated conidia at high humidity-low humidity results in enhanced survival as does oil formulation of the conidia.

Example 5

Previous research has demonstrated that oil formulated conidia have excellent long-term (>50% viability after >3 months) survival on glass and clay surfaces at 26° C. (Darbro and Thomas, American Journal of Tropical Medicine and Hygiene 80, 992-997 (2009); Blanford et al., Lethal and pre-lethal effects of a fungal biopesticide contribute to substantial and rapid control of malaria vectors. PLoS One. 6(8): e23591 (2011). This indicates that conidia are likely to remain viable for an extended period of time in environments found in human dwellings. Furthermore, Darbro and Thomas used airborne spore monitoring to demonstrate that oil formulations of fungal conidia do not result in liberation of significant numbers of conidia when pre-sprayed onto cloth and placed indoors.

Figure 10:
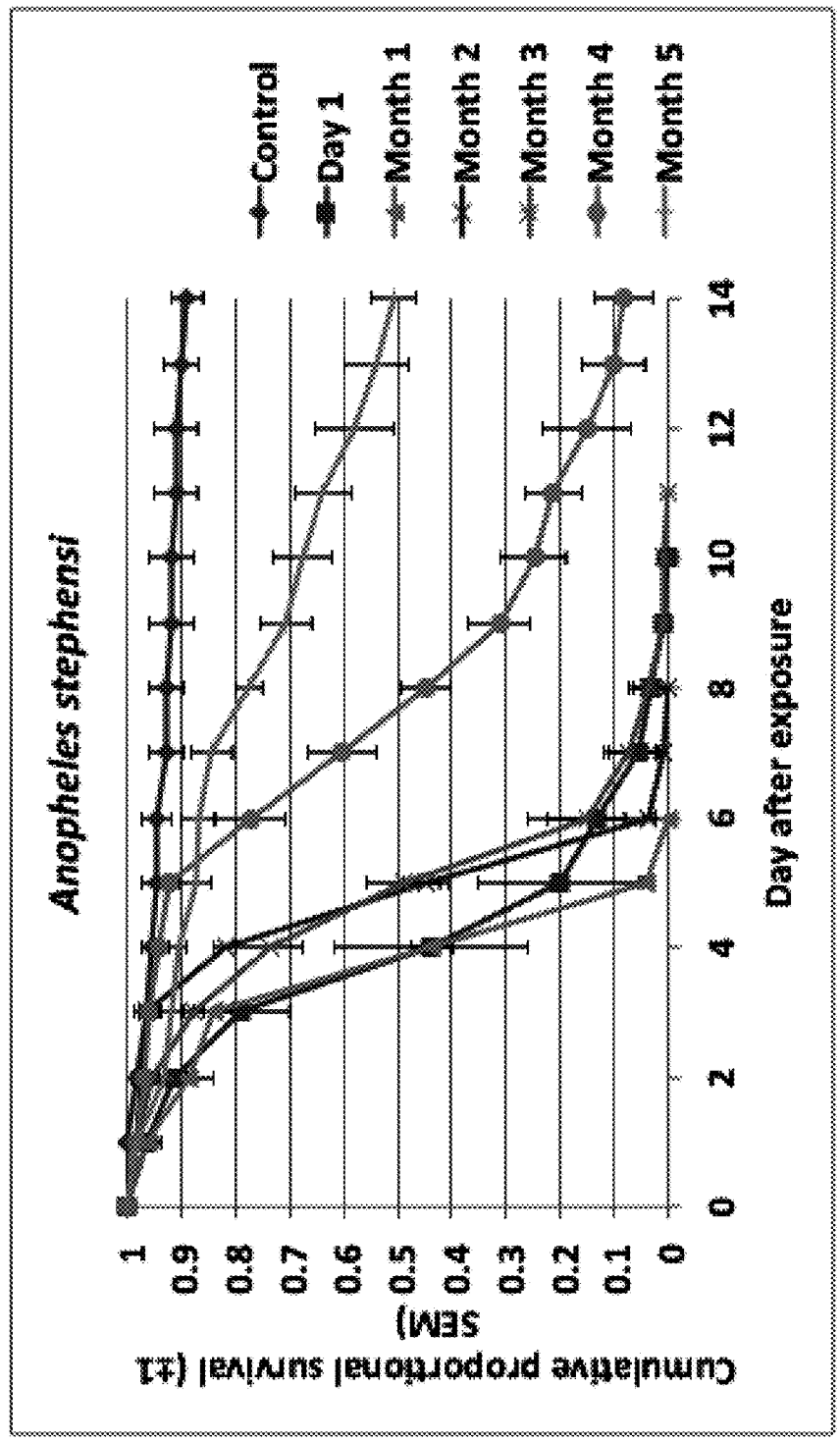
FIG. 10 is a graph showing the infectivity of spray residue of *B. bassiana* over time according to embodiments of the invention.

The infectivity of spray residue of the *Beauveria bassiana* conidia on clay tiles was also evaluated. The conidia on clay tiles were stored at 26 C and 80% humidity. The graph depicted in FIG. 10 shows susceptibility of mosquitoes to the *Beauveria bassiana* conidia. The spray residue remains 100% effective for 3 months, declining in efficacy after 4 months in conditions less favorable than typically found in houses in the US. As depicted the mosquitoes are less susceptible to *B. bassiana* (100% kill in 6 days) than bed bugs (100% kill in 4 days).

Example 6

Additional bioassays of oil formulated conidia were evaluated to determine the effect of temperature on the conidia formulations. The methods of Example 1 were followed to evaluate the effects of temperate on oil formulated conidia of *Beauveria bassiana* (strain 193-825) in comparison to oil formulated conidia of *Metarhizium anisopliae* (strain ESF1) on the survival of bed bug populations in comparison to control bed bug populations without any conidia from any entomopathogenic fungi.

Figure 11A:
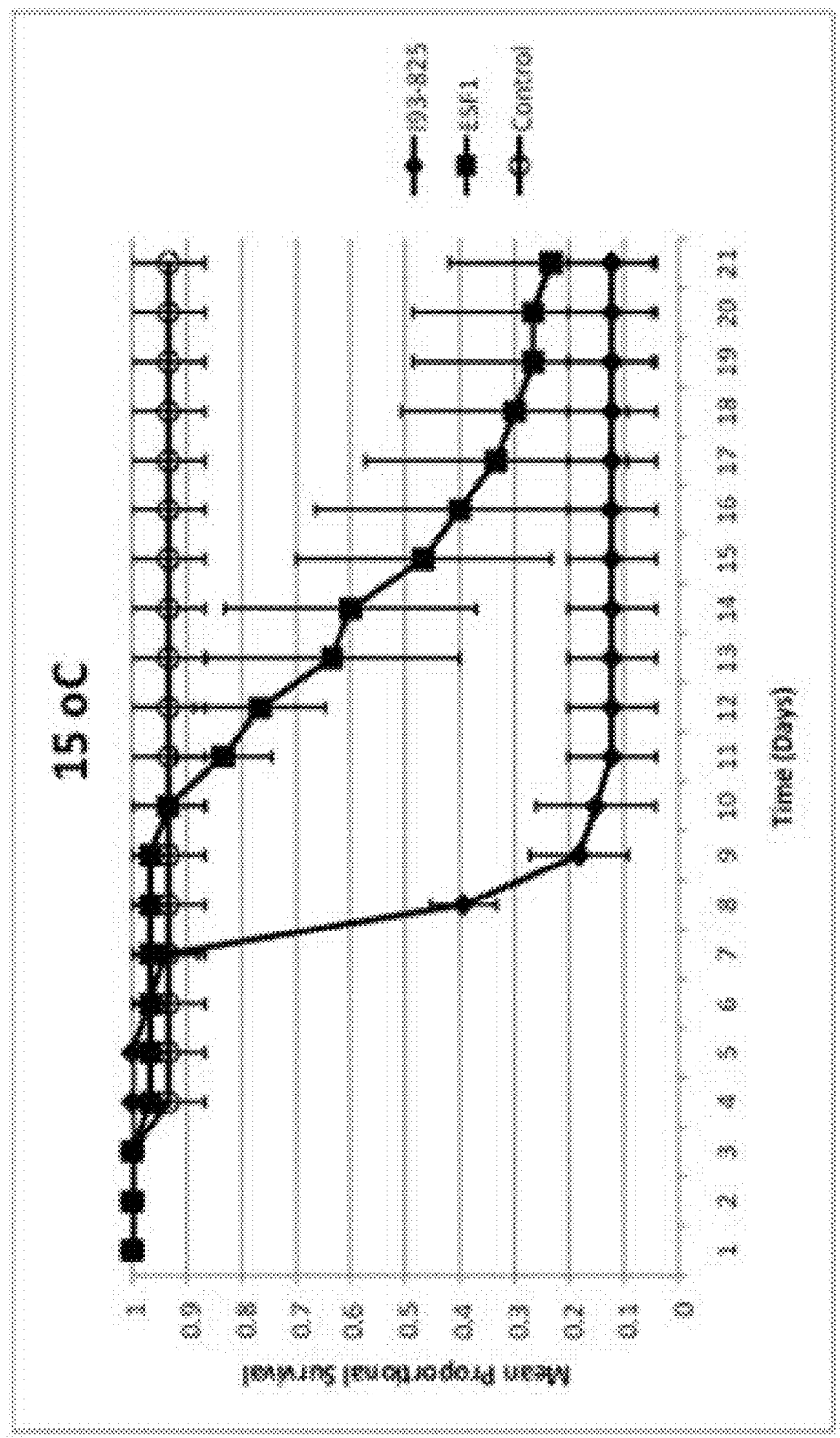
FIGS. 11A-D are graphs showing the mean survival of bed bug populations decrease with exposure to increased temperature according to an embodiment of the invention.
Figure 11B:
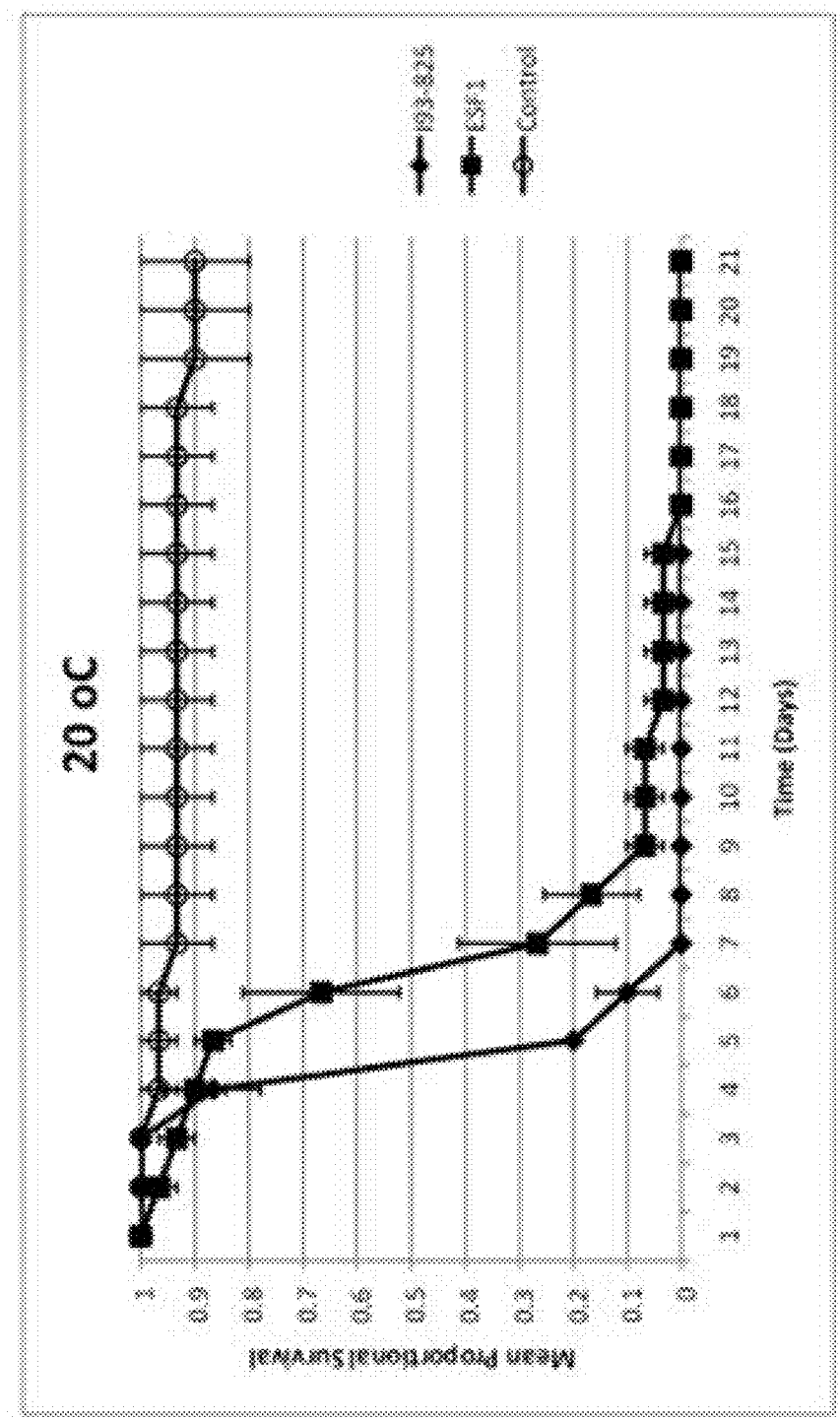
Figure 11C:
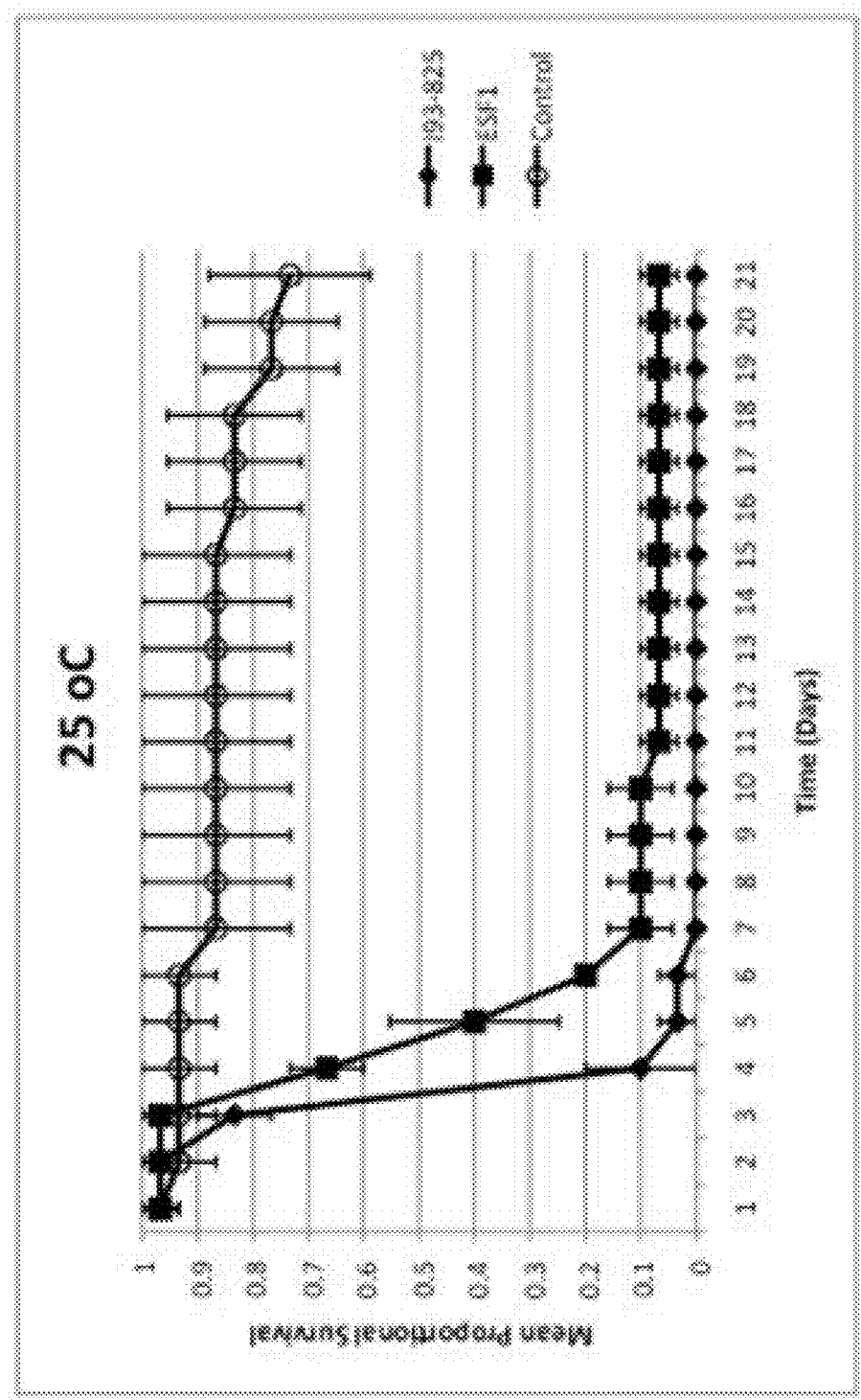
Figure 11D:
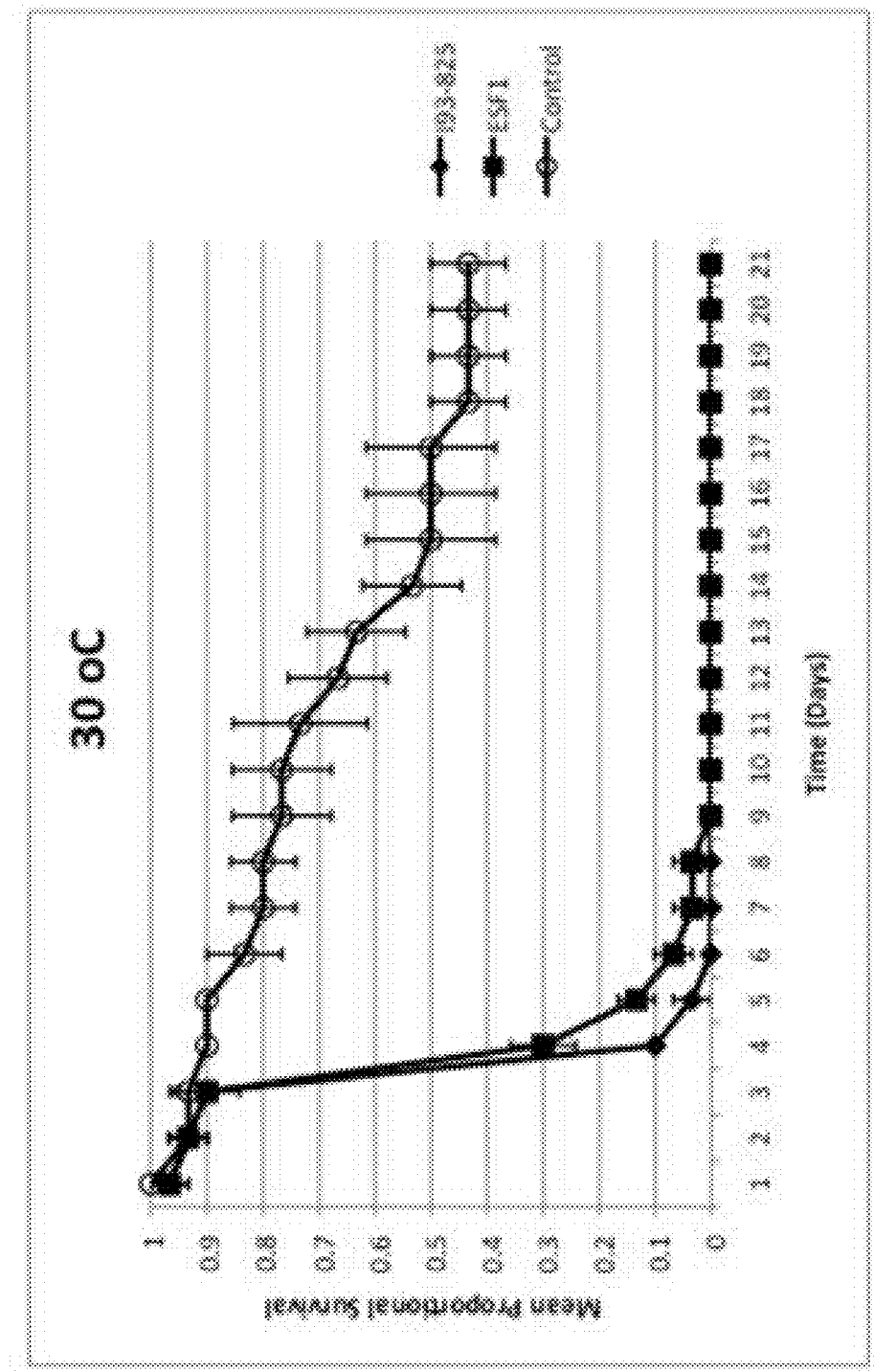

Overall, FIGS. 11A-D show that mean survival of bed bug populations decrease with exposure to increased temperature (see control populations in FIG. 11A (15 C) compared to FIG. 11D (30 C), wherein control population survival decreases with the increase in ambient temperature. Similarly, the survival of both conidia strains showed improved results when employed at increased temperature of 30 C over 15 C. However, the *Beauveria bassiana* strain outperformed the *Metarhizium anisopliae* strain at all temperatures evaluated.

As shown in FIGS. 11A-D, the mean proportional survival of bed bug populations exposed to cotton jersey sprayed with oil formulated conidia of *Beauveria bassiana* I93-825 (diamonds) or *Metarhizium anisopliae* ESF1 (squares) for 1 hour, then removed and incubated at 15, 20, 25 or 30° C. for 21 days.

Example 7

Additional data on conidia spore transfer or pick-up by bed bug populations from differing substrate surfaces were further evaluated. The methods of Example 1 were followed to evaluate the effects of substrate surface texture/type on the mean proportional survival of harborage populations based on horizontal transmission of the conidia of *Beauveria bassiana* (strain 193-825) (applied at a rate of $3 \times 10^6$ conidia/$cm^2$ using an airbrush sprayer). The following surfaces were coated according to Example 1 with the conidia of *Beauveria bassiana* (strain 193-825): paper, jersey, crib sheet, towel. The surfaces were treated and placed within petri dishes, such that the entire petri dish was covered with the treated surfaces and bed bugs placed in the petri dishes have constant contact with the treated surface in order to maximize exposure to the conidia. The bed bugs were contained on the treated surfaces for 1 hour. The methods employed the exposure of 5 bed bugs from each population which where the provided to artificial harborages containing an additional 20 bed bugs (unexposed to the conidia of *Beauveria bassiana*).

Figure 12:
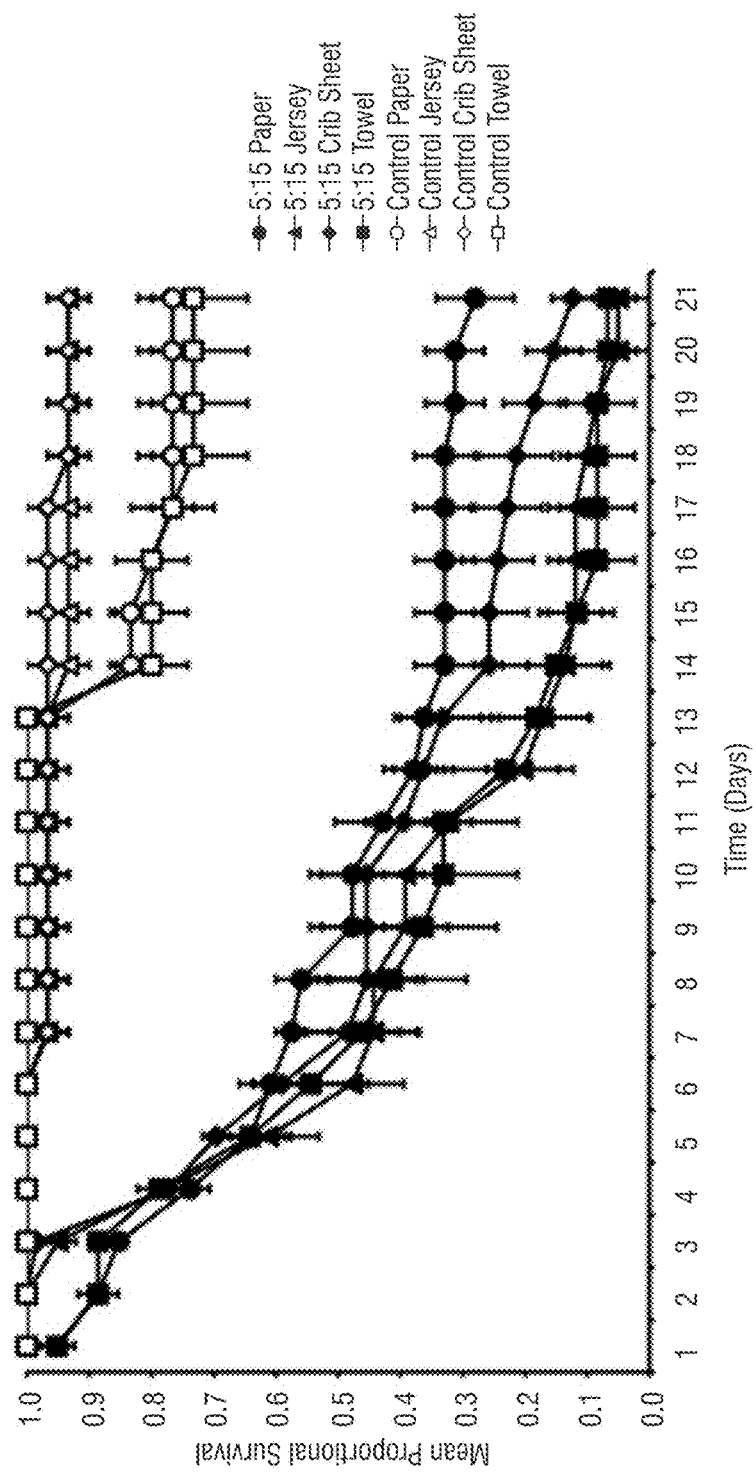
FIG. 12 is a graph showing mean survival of bed bug populations within an artificial harborage significantly decrease as a result of the horizontal transmission of the conidia of *Beauveria bassiana*, which is further dependent on the type of substrate surface treated with the conidia according to an embodiment of the invention.

As shown in FIG. 12, Mean proportional survival of populations of 20 bed bugs following exposure of 5 individuals from each population to paper (circles), cotton jersey (triangles), terry crib sheet (diamonds) or towel (squares), sprayed with an oil formulation of *B. bassiana* 193-825 for 15 minutes. Exposed bed bugs were added to 15 untreated bed bugs in folded paper harborages and incubated at 25° C. for 21 days.

Overall, FIG. 12 shows that mean survival of bed bug populations within an artificial harborage significantly decrease as a result of the horizontal transmission of the conidia of *Beauveria bassiana* according to the embodiments of the invention. The results further indicate that the more texturized substrate surfaces (towel and jersey) provide the bed bugs with the greatest amount of horizontal transmission. Without being limited to a particular theory of the invention, the substrate surface with more texture slow the rate of a bed bug crossing such surface, thereby increasing the exposure and retention/pick-up of the conidia onto the bed bug body. Thereafter, the bed bug serving as a vector for horizontal transmission of the conidia of *Beauveria bassiana* into the harborage population delivers more viable conidia spores for eradicating the harborage population.

Example 8

The data generated according to Example 7 was further investigated to confirm the impact on exposure time of a bed bug to the treated substrate surface with the percent survival of bed bug populations. Example 7 exposed bed bugs to the conidia spores for 1 hour. In these subsequent methods the exposure time was significantly reduced to either a fixed time of 15 minutes or 1 minute of cumulative movement (conidia still applied at a rate of $3 \times 10^6$ conidia/$cm^2$ using an airbrush sprayer). Bed bugs were placed on treated surfaces (*Beauveria bassiana* 193-825) of either paper, jersey, crib sheet or a towel (consistent with Example 7) for either 15 minutes or 1 minute. Notably, in the 1 minute exposure, the time of exposure was only counted during periods of activity when the bed bugs were moving across the surfaces to ensure that the time period reflects actual exposure to the conidia whilst traversing a treated surface (barrier) and opportunity for the bed bugs to pick up conidia spores for such horizontal transmission to other bed bugs within a harborage. Thereafter, the bed bugs were removed from the treated (or control) surfaces and incubated at 25° C. for 21 days.

Figure 13A:
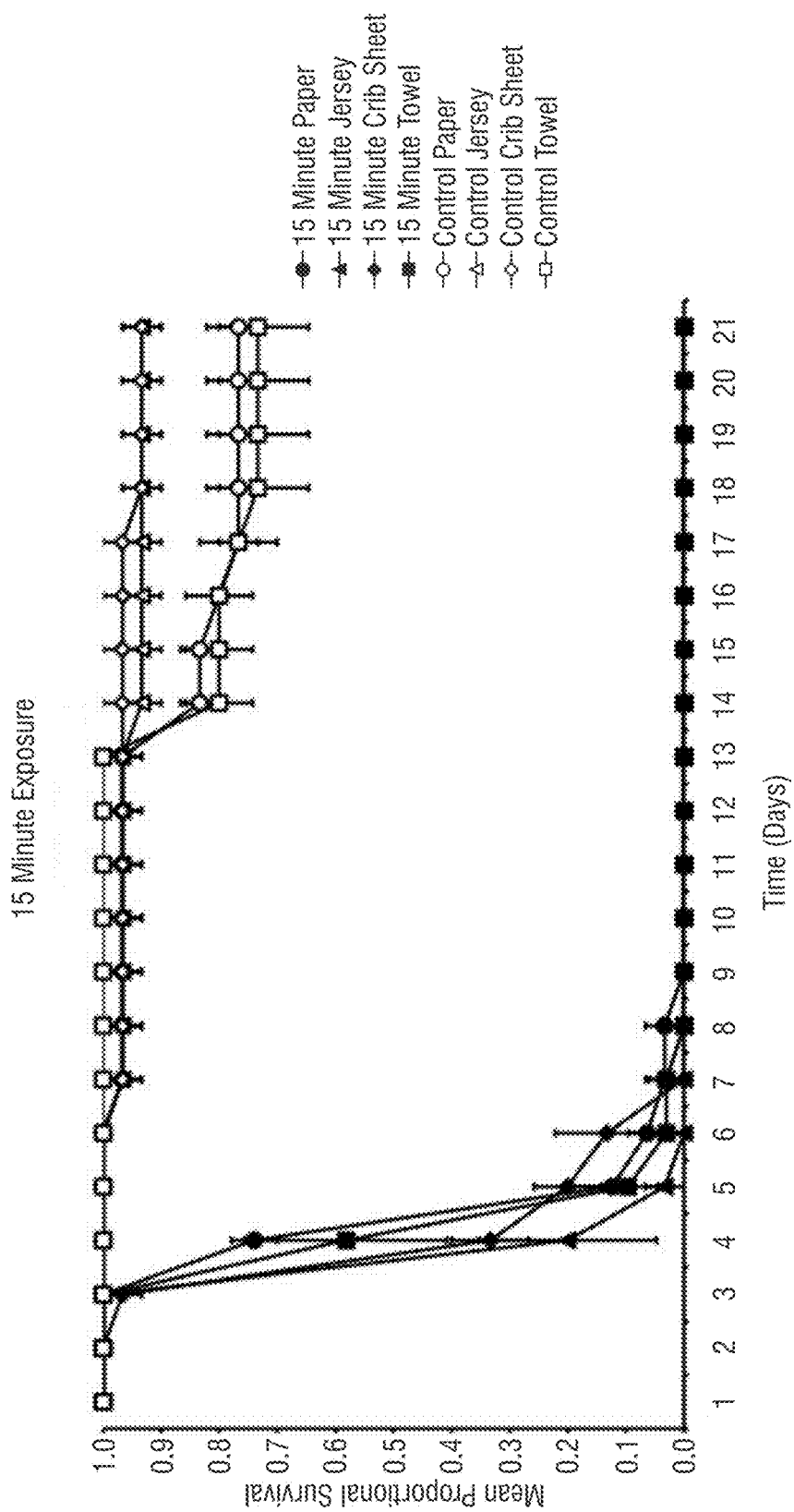
FIGS. 13A-B are graphs showing the relationship between proportional survival of bed bugs and the length of exposure time to various substrate surfaces treated with *B. bassiana* according to embodiments of the invention.
Figure 13B:
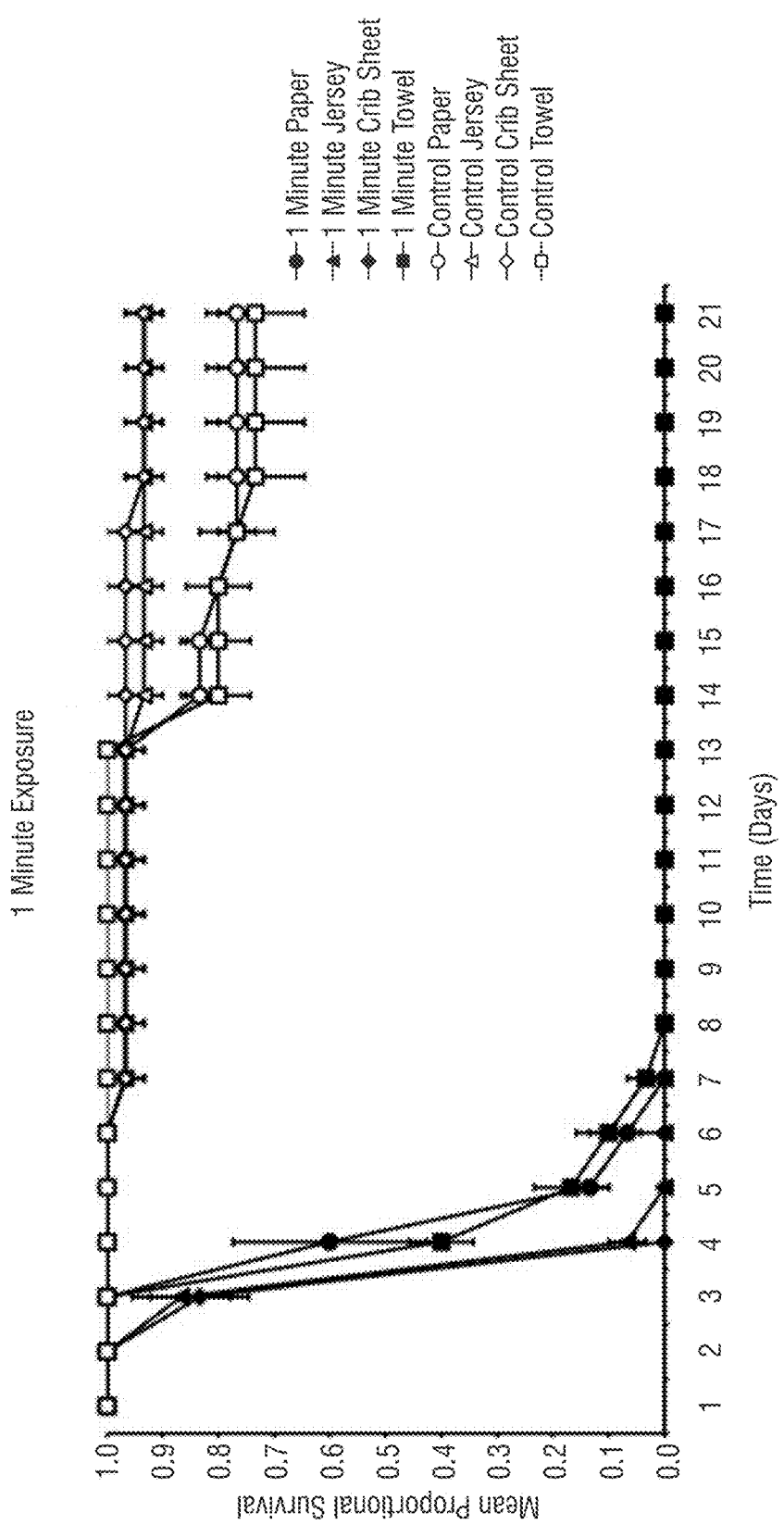

The mean proportional survival of the bed bug populations that were exposed to the various substrate surfaces were evaluated after the 21 day incubation period. As shown in FIGS. 13A-B, bed bugs exposed to all of the treated surfaces (*Beauveria bassiana* 193-825) completely eradicated the bed bug populations after 9 days, regardless of the time of exposure to the conidia spores. However, as shown in FIG. 13B, the rate of decrease in bed bug survival was slightly improved with the shorter exposure time of 1 minute of cumulative movement.

Example 9

Additional data was generated to evaluate the average speed of movement of bed bug populations over various substrate surfaces in relation to the developmental stage of the bed bugs. Bed bugs were placed individually at the center of a 20 cm diameter circle of each test substrate evaluated in Examples 7 and 8. The bed bugs were visually monitored to determine their activity on the surfaces, including their speed of traversing the surface. $1^{st}$ instars were unable to be included in the towel experiment as the bed bugs were too small to see moving on the towel surface.

Figure 14:
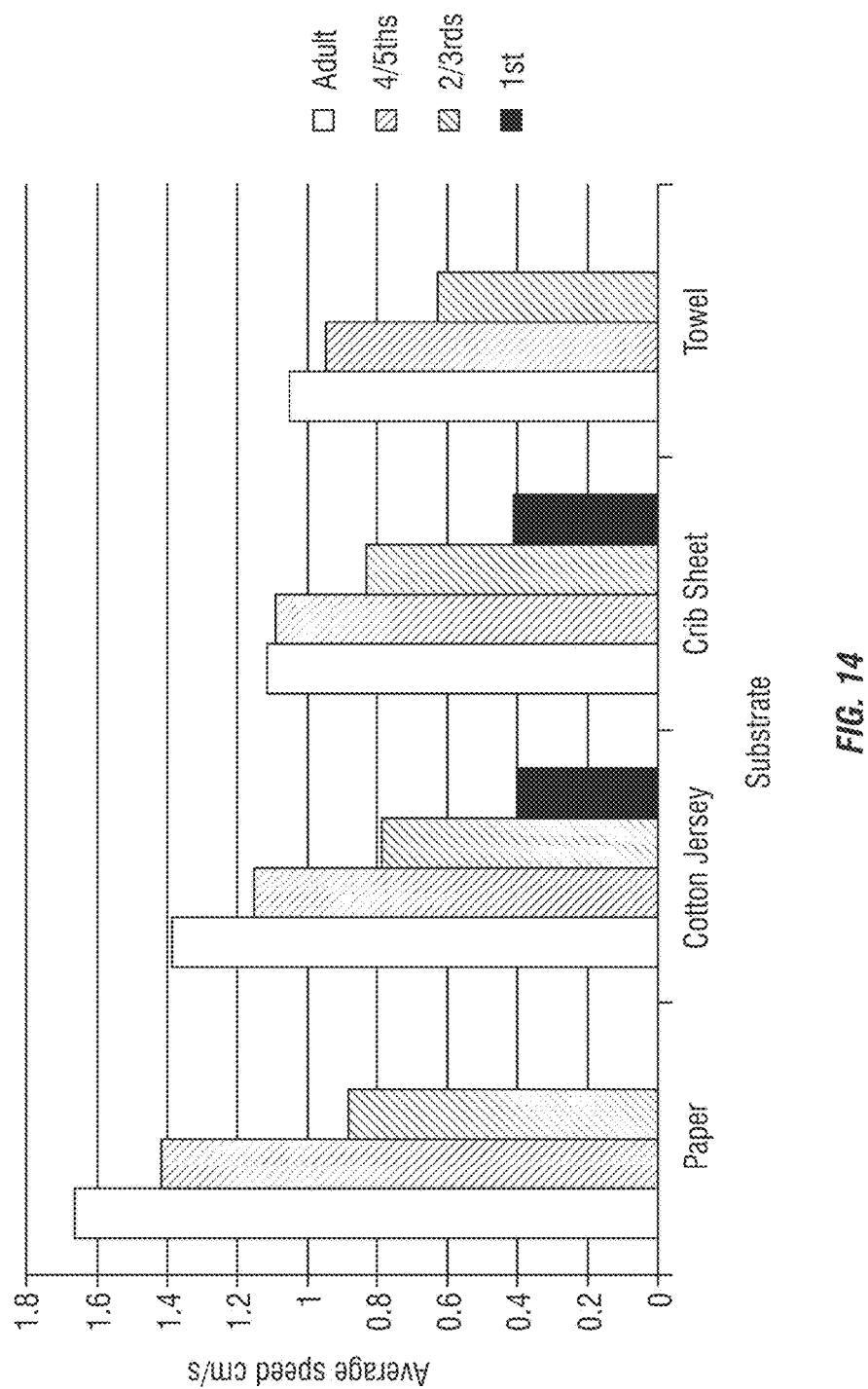
FIG. 14 is a graph showing the impact on the speed of bed bugs traversing various substrate surfaces according to an embodiment of the invention.

Visual observations indicated that the bed bugs instinctively moved away from the center of the circle to the edges of each surface. Each bed bug was timed over a distance of 5 cm with three repetitions per bug and 15 bugs per treatment. The average speed for each life stage and substrate was calculated from a total of 45 measurements. The results are shown in FIG. 14. As shown in FIG. 14, the adult bed bugs traveled at the greatest speed, with each less developed instar population traveling at slower rates. The data further supports the efficacy of the compositions and methods of the invention in mixed populations of bed bugs. Any bed bugs able to traverse a barrier treatment composition according to the invention are exposed to conidia spores and can further horizontally transmit the spores to other bed bug populations.

Example 10

Data on spore viability on various surfaces was further evaluated. Oil formulations of conidia of *B. bassiana* (193-825 batch PSU 37) where made and then evaluated on both glass slides and plastic sheetings. The viability of oil formulated conidia of *B. bassiana* on glass slides and plastic sheeting following application with an airbrush and storage at 26±1 C was evaluated.

Figure 15:
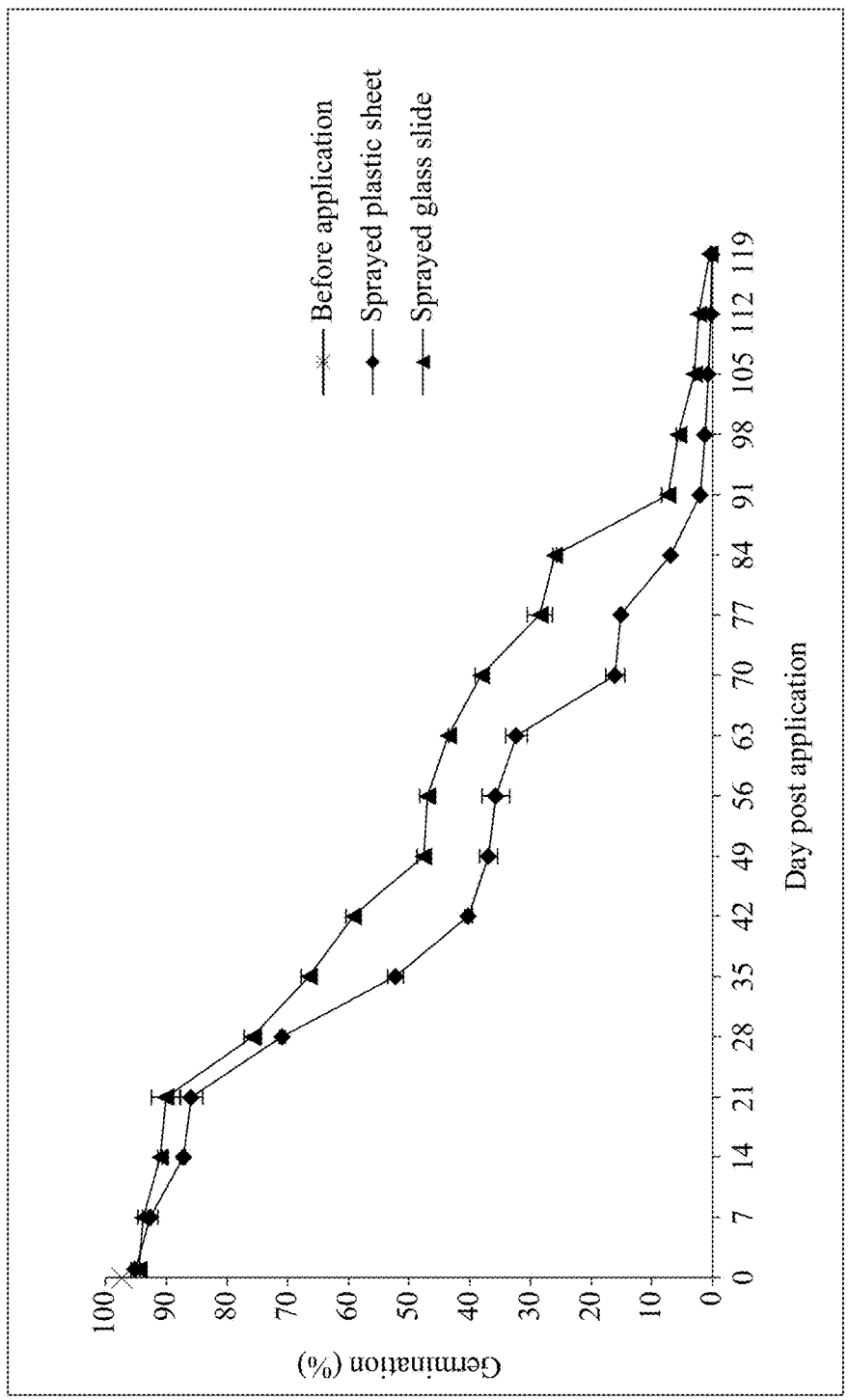
FIG. 15 is a graph showing the viability of oil formulated conidia of *B. bassiana* according to an embodiment of the invention.

As shown in FIG. 15, although the percent of germination of the conidia decreased significantly after 3 weeks, the experimentation was conducted at 26±1 C and elevated temperatures provide more hostile environment for conidia stability, wherein each degree Celsius increase has a detrimental impact on stability. Therefore, the percent germination would maintain sufficient levels (such as above about 90%) for periods longer than 3 weeks at lower temperature ranges.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A method for controlling bed bugs using a biopesticide comprising:
    applying onto a substrate surface a biopesticide composition comprising viable conidia of entomopathogenic fungi formulated in oil or an oil-based aqueous mixture or suspension, to provide a treated substrate surface having a concentration of at least 100 conidia/cm$^2$;
    wherein the biopesticide composition is applied to the substrate surface at a location between a bed bug harborage and a lure, which attracts bed bugs to cross the treated substrate surface and thereby the conidia attach to, and infect the bed bugs.

2. The method of claim 1, wherein said biopesticide composition is odorless.

3. The method claim 1, wherein the treated substrate surface has a concentration between about 3×10$^3$ conidia/cm$^2$ to about 3×10$^{10}$ conidia/cm$^2$.

4. The method of claim 1, wherein said biopesticide composition does not include pre-sporulation entomopathogenic fungi.

5. The method of claim 1, wherein the substrate surface is a substrate surface in a bedroom.

6. The method of claim 5, wherein the substrate surface in the bedroom is a substrate surface of a bed frame, headboard, door or window trim, light switch, baseboard, mattress, carpet, furniture, linen, dust ruffle, or bedding.

7. The method of claim 1, wherein the conidia on the treated substrate surface are viable for up to 3 months.

8. The method of claim 1, further comprising routinely applying the biopesticide composition to the substrate surface.

9. The method of claim 1, further comprising providing a living human lure to attract bed bugs to cross the treated substrate surface.

10. A method for controlling bed bugs using a biopesticide comprising:
    applying to a substrate surface a biopesticide composition comprising viable conidia of Deuteromycete fungi formulated in oil or an oil-based aqueous mixture or suspension, to provide a treated substrate surface having a concentration of at least 100 conidia/cm$^2$;
    wherein the biopesticide composition is applied to the substrate surface at a location between a bed bug harborage and a lure, which attracts bed bugs to cross the treated substrate surface and thereby the conidia attach to, and infect the bed bugs.

11. The method of claim 10, wherein the treated substrate surface has a concentration between about 3×10$^3$ conidia/cm$^2$ to about 3×10$^{10}$ conidia/cm$^2$.

12. The method of claim 10, wherein said biopesticide composition is odorless.

13. The method of claim 10, wherein the infected bed bugs are killed within 10 days.

14. The method of claim 10, wherein the substrate surface is a substrate surface in a bedroom.

15. The method of claim 10, further comprising providing a living human lure to attract bed bugs to cross the treated substrate surface.

16. A method for controlling bed bugs using a biopesticide comprising:
   coating onto a substrate surface in a bedroom viable conidia of entomopathogenic fungi to provide a treated substrate surface having a concentration of at least 100 conidia/cm$^2$; and
   attracting bed bugs to cross the treated substrate surface and thereby the viable conidia of entomopathogenic fungi attach to, and infect the bed bugs.

17. The method of claim 16, wherein the viable conidia are harvested from *Beauveria, Lecanicillium, Verticillium, Metarhizium, Paecilomyces*, or *Akanthomyces*.

18. The method of claim 16, wherein the substrate surface in the bedroom is a substrate surface of a bed frame, headboard, door or window trim, light switch, baseboard, mattress, carpet, furniture, linen, dust ruffle, or bedding.

19. The method of claim 16, wherein the conidia on the treated substrate surface are viable for up to 3 months.

\* \* \* \* \*

UNITED STATES PATENT AND TRADEMARK OFFICE
CERTIFICATE OF CORRECTION

PATENT NO. : 10,085,436 B2
APPLICATION NO. : 14/810137
DATED : October 2, 2018
INVENTOR(S) : Nina E. Jenkins et al.

Page 1 of 1

It is certified that error appears in the above-identified patent and that said Letters Patent is hereby corrected as shown below:

In the Specification

On Column 1, Line 11, before the "FIELD OF INVENTION", please insert the following paragraph:
-- STATEMENT REGARDING FEDERALLY SPONSORED RESEARCH OR DEVELOPMENT
This invention was made with government support under Hatch Act Project Nos. PEN04067 and PEN04136 awarded by the United States Department of Agriculture. The Government has certain rights in the invention. --

Signed and Sealed this
Twentieth Day of August, 2019

Andrei Iancu
*Director of the United States Patent and Trademark Office*